United States Patent
Muller-Feuga et al.

(10) Patent No.: US 8,822,199 B2
(45) Date of Patent: Sep. 2, 2014

(54) REACTION JACKET FOR A PHOTOSYNTHETIC REACTOR AND RELATED PHOTOSYNTHETIC REACTOR

(75) Inventors: Arnaud Muller-Feuga, Baillargues (FR); Michel Lemar, Saint Symphorien d'Ozon (FR)

(73) Assignee: Microphyt (FR)

( * ) Notice: Subject to any disclaimer, the term of this patent is extended or adjusted under 35 U.S.C. 154(b) by 963 days.

(21) Appl. No.: 12/908,358

(22) Filed: Oct. 20, 2010

(65) Prior Publication Data

US 2011/0111484 A1 May 12, 2011

Related U.S. Application Data

(60) Provisional application No. 61/259,704, filed on Nov. 10, 2009.

(51) Int. Cl.
| | | |
|---|---|---|
| *B29C 47/00* | (2006.01) | |
| *C12M 1/09* | (2006.01) | |
| *C12M 1/16* | (2006.01) | |
| *C12N 1/12* | (2006.01) | |
| *B29D 22/00* | (2006.01) | |
| *C12M 1/00* | (2006.01) | |
| B29C 53/48 | (2006.01) | |
| B29L 23/00 | (2006.01) | |
| B29C 43/24 | (2006.01) | |
| B29C 65/00 | (2006.01) | |

(52) U.S. Cl.
CPC ................ *C12M 21/02* (2013.01); *B29C 53/48* (2013.01); *C12M 23/26* (2013.01); *B29L 2023/001* (2013.01); *C12M 23/34* (2013.01); *B29C 47/0023* (2013.01); *B29C 2791/007* (2013.01); *C12M 23/56* (2013.01); *B29C 43/24* (2013.01); *B29C 66/4322* (2013.01); *C12M 23/22* (2013.01); *B29C 47/00* (2013.01)
USPC ...................... 435/257.1; 435/292.1; 156/213

(58) Field of Classification Search
CPC ... B29C 47/0023; C12M 21/02; C12M 23/22; C12M 23/26; C12M 23/34; C12M 23/56
USPC ................................ 435/257, 292.1; 156/213
See application file for complete search history.

(56) References Cited

U.S. PATENT DOCUMENTS

| 4,868,123 A | 9/1989 | Berson et al. | |
|---|---|---|---|
| 2009/0305389 A1* | 12/2009 | Willson et al. | ............. 435/257.1 |

FOREIGN PATENT DOCUMENTS

| ES | 2150389 A1 | 11/2000 |
|---|---|---|
| ES | 2193860 A1 | 11/2003 |

(Continued)

*Primary Examiner* — Nathan Bowers
*Assistant Examiner* — Gautam Prakash
(74) *Attorney, Agent, or Firm* — Cantor Colburn LLP

(57) ABSTRACT

Reaction jacket for a photosynthetic reactor, configured to float on an expanse of water and to define a gas/liquid culture medium diphasic flow path between first and second openings of the reaction jacket, the jacket including two sheaths, outer and inner, respectively, at least partially made from a material transparent to light radiation, the inner sheath extending inside the outer sheath such that these sheaths define an inter-sheath space between them in fluid connection with the first opening of the jacket, where the outer sheath has an open proximal end and a closed distal end, and the inner sheath has an open proximal end in fluid connection with the second opening of the jacket and a distal end provided with at least one communication orifice between the inside of the inner sheath and the inter-sheath space.

14 Claims, 9 Drawing Sheets

(56) References Cited

FOREIGN PATENT DOCUMENTS

| | | |
|---|---|---|
| FR | 2324224 | 4/1977 |
| FR | 2361060 A1 | 3/1978 |
| FR | 2685344 A1 | 6/1993 |
| FR | 2875511 A3 | 3/2006 |
| GB | 2118572 | 11/1983 |
| GB | 2331762 | 6/1999 |
| WO | 2008134010 A2 | 11/2008 |
| WO | WO 2008/134010 * | 11/2008 |
| WO | 2009051479 | 4/2009 |
| WO | 2009090549 | 7/2009 |

* cited by examiner

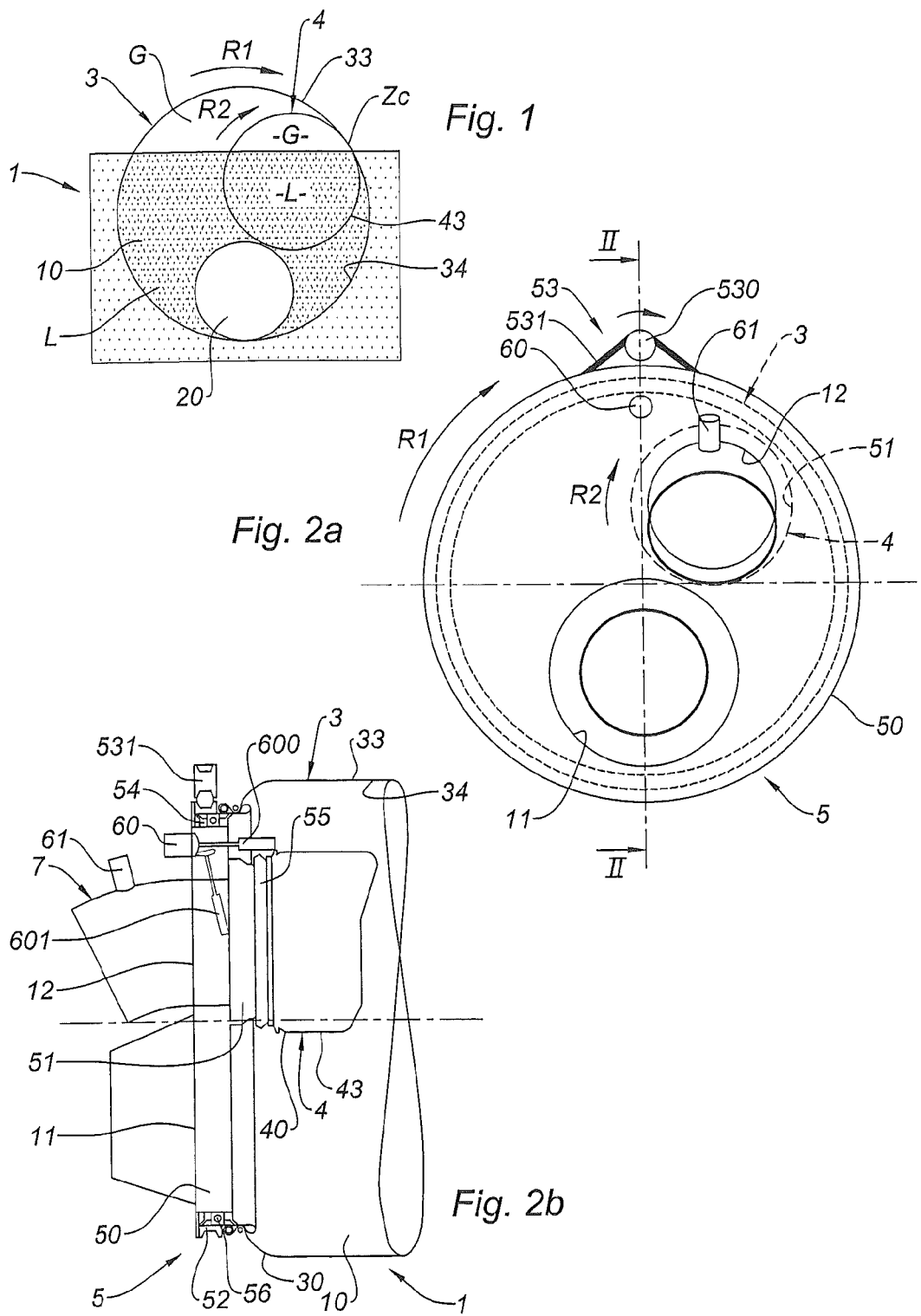

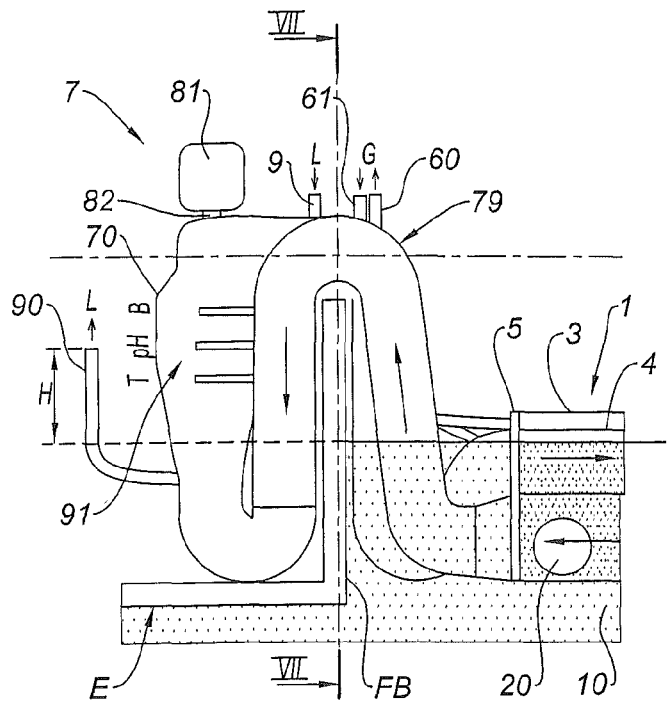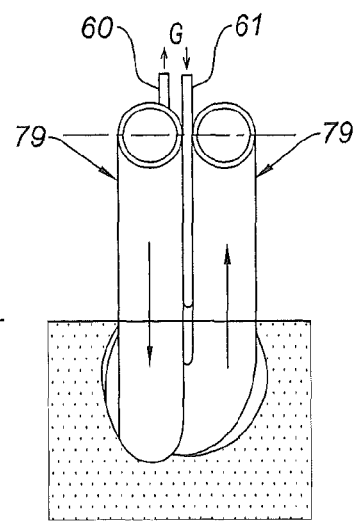
Fig. 7a
Fig. 7b
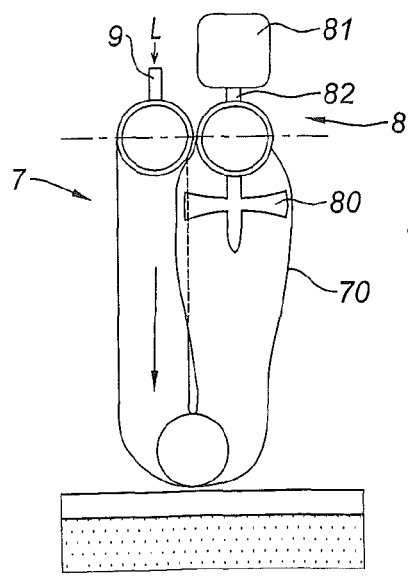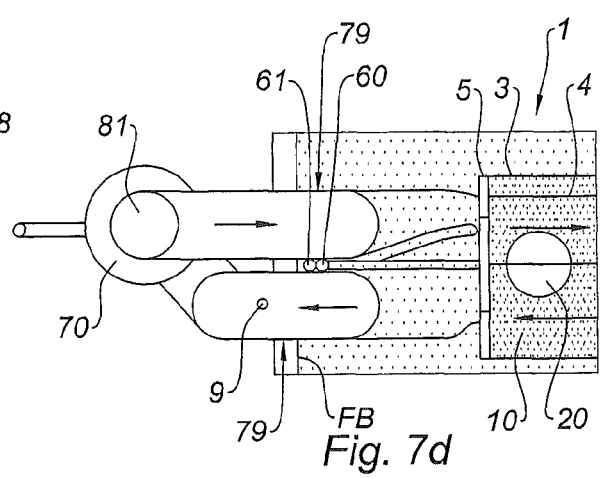
Fig. 7c
Fig. 7d

REACTION JACKET FOR A PHOTOSYNTHETIC REACTOR AND RELATED PHOTOSYNTHETIC REACTOR

TECHNICAL FIELD

The present invention concerns a reaction jacket for a photosynthetic reactor adapted for growing photosynthetic microorganisms, in particular algae, a method for producing such a reaction jacket, a related photosynthetic reactor, and a method for growing photosynthetic microorganisms using such a reactor.

It more particularly concerns a reaction jacket designed, on one hand, to float on an expanse of water and, on the other hand, to define a gas/liquid culture medium diphasic flow path between first and second openings of said reaction jacket.

BACKGROUND

The present invention is applicable to growing any photosynthetic organism, i.e. any life form likely to develop and photosynthesize in a suitable nutritional culture medium, in the presence of solar radiation and carbon-rich gas, such as carbon dioxide, microalgae being the primary representatives of this life form.

The analysis of the compared performance of the photosynthetic organisms leads to favoring the growth of microalgae, which are the oldest players in photosynthesis on our planet. Unlike upright plants, they do not have any complex member with a long construction time to access water and light. They do not need to stiffen their stems using metabolites (cellulose, lignin) that are difficult to decompose. Increased effectiveness of the microalgae cultures follows, translating to surface productivities that can reach 100 tons (dry weight) per hectare and per year versus 10 tons for the best field plants. All of the biomass is usable, whereas large-scale farming harvests generally only concern grains, with the exception in particular of sugarcane and forage plants that leave at least the root system in place.

More particularly, the photosynthetic microorganisms concerned by the invention include aquatic plants such as, for example, microalgae, moss protonemas, small microalgae, and isolated cells of multicellular plants. These aquatic plants have interesting properties in particular in fields such as pharmacy, human and animal nutrition, dermo-cosmetology, energy, and the environment.

As for most photosynthetic microorganisms, access to this resource consists essentially of assisted growth in adapted reactors. Light being their main substrate, the culture medium must have an optical interface receiving a light flow. The difficulty of cultivating photosynthetic microorganisms is related to the fact that they themselves constitute obstacles to the passage of light, which is their main substrate. The growth of the culture will therefore stabilize when the light no longer penetrates the thickness of the culture. This phenomenon is called self-shadowing.

The light path length makes it possible to characterize the different confinement modes, and is defined as:

the length the light travels from its entry into the culture through a transparent optical interface to an opposite opaque wall; or half the distance separating the two transparent optical interfaces when the confinement receives the light by two opposite transparent optical interfaces.

This light path length varies between a few centimeters and a few decimeters and mainly determines the production of biomass per unit of time and optical surface (surface productivity in $g/m^2/d$) and the concentration of the culture (en g/L) in the final growth phase. The different confinement modes that are implemented to ensure the growth of small aquatic plants can thus be classified as a function of this characteristic length.

The photosynthesis reaction is also accompanied by a consumption of carbon dioxide ($CO_2$) and oxygen production. The excess oxygen inhibits the reaction, while the absence of carbon dioxide interrupts it for lack of substrate to transform. A gas/liquid interface must therefore be developed for mass transfers between these gases and the liquid phase. In order to favor these exchanges and avoid heterogeneities, the culture must be the seat of a mixture intended to renew the organisms at the aforementioned optical interface and also at this gas/liquid interface.

A first known embodiment of a photosynthetic reactor consists of an open container of the basin or tray type where the culture is kept by gravity and has a free surface making the optical interface and the liquid/gas interface by itself. The culture is mixed inside the basin by one or several mechanical stirring devices, for example of the vaned rotor type. The cultures in the basin thus realized can cover significant surfaces and this embodiment is at the origin of the majority of current world microalgae production, which reaches several thousands of tons in dry weight. The photosynthetic organisms produced by this type of reactor are essentially:

so-called extremophilic algae whereof the mediums are hostile to predators and competitors, such as for example algae of the *spirulina* or *Dunaliella* type; or so-called dominant algae that support mechanical stresses or contaminations better than the others, such as, for example, algae of the *Chlorella, Scenedesmus, Skeletonema, Odontella* or *Nannochloropsis* types.

A second known embodiment of a photosynthetic reactor also consists of an open container of the tank or tray type, but whereof the dimensions are smaller than those of the basins of the first known embodiment. These containers generally have lateral walls transparent to solar radiation, such that the optical interface is made up both of the free surface of the liquid medium and by the transparent lateral walls.

In this second embodiment, it is traditional to use an injection of air done in the lower portion of the tank, which leads to the formation of air bubbles rising in the liquid up to the free surface. The surface of the bubbles thus formed constitutes the gas/liquid interface. While rising to the surface, the bubbles pull the culture upwards, thereby creating convective movements that can extend to the entire volume. Carbon dioxide ($CO_2$) is sometimes added to the injected air to contribute additional carbon according to a predefined molar fraction of several percent.

The tanks of the second known embodiment, which have a smaller volume than the basins of the first embodiment, are adapted to more controlled cultures, in particular microalgae cultures intended for the nutrition of mollusk larvae or live prey of fish larvae in aquaculture. Frequent cleaning of these tanks as well as pure and massive inoculation make it possible to limit contaminations inside the tank. The microalgae thus grown, of which there are several dozen species, have relatively close temperature and light needs that make it possible to grow them in shared areas.

These two embodiments in the form of an open container offer a light path length of one to several decimeters.

A third known embodiment of a photosynthetic reactor consists of a closed reactor, so-called photobioreactor, comprising a closed loop inside which the liquid culture medium circulates, said closed loop comprising a reaction channel provided with reaction sections made of a material transparent to light radiation (or light), and a closing channel ensuring the connection between the two opposite ends of the reaction channel.

Photobioreactors, described in particular in documents GB 2 118 572 A, ES 2 193 860 A1, GB 2 331 762 A, ES 2 150 389 A1, FR 2 685 344 A1 and FR 2 875 511 A3, offer substantially smaller light path lengths, in the vicinity of one to several centimeters, in relation to the embodiments with an open container, and they make it possible to achieve concentrations of photosynthetic organisms of several grams per liter sheltered from airborne contamination. The reaction channel of the photobioreactors generally consists of transparent plates or tubes, made of glass or plastic, with a thickness or diameter in the vicinity of a centimeter, that are connected end to end by bends to form a winding channel together.

The closing channel comprises a so-called ascending vertical tube, in which the liquid medium rises, and a descending vertical tube in which the liquid medium descends under the effect of gravity.

The gas injection system generally implemented in photobioreactors consists of an airlift, also called gas-lift, i.e. through a gas injection at the base of an ascending vertical tube of the closing channel, said gas injection serving both to circulate or move the liquid reaction medium and perform the gas-liquid exchanges. The gas-lift includes, in the upper portion, a widened gravity tank or volume in which the lower circulation speeds allow the gas-liquid separation, and the descending vertical tube of the closing channel emerges in the bottom of the gravity tank to supply the reaction channel with liquid.

The aforementioned photobioreactors apply the principle that the reaction only takes place in the liquid phase, in other words these photobioreactors seek to minimize the volume of gas injected into the reactor so as not to decrease the volume of the liquid culture medium by as much, out of a concern for not decreasing production. Thus, in these photobioreactors, oxygen is extracted using a vertical ascending tube defined above, said vertical ascending tube forming an air bubble column emerging in the gravity tank receiving the liquid culture medium, and including a gas injection in the lower portion, opportunely of CO2-enriched air. As described above, the circulation and gas transfer functions are combined within this single device, called gas-lift, which creates an ascending vertical circulation by movement quantity exchange between the liquid mass and the gas bubbles resulting from the injection. The supersaturated photosynthetic oxygen in the liquid moves to the gas phase by air sweeping, while the $CO_2$ goes to solution. These degassing and carbonation phases are essential and take place simultaneously and indissociably at this single device in which the culture must pass at a high frequency to prevent a deleterious increase in the dissolved oxygen content.

Gas-lifts have the drawback of generating gas bubbles that rise in the vertical ascendant tube of the closing channel of the photobioreactors. The applicant has in fact observed the deleterious role of these bubbles for the microorganism culture in the photobioreactors:

on one hand, the bubbles mechanically stress the microalgae and can harm fragile microorganisms; and on the other hand, the bubbles capture, through tensioactive effect, the molecules that have tensioactive properties, and in particular organic molecules, cellular debris, and the excretion products of living cells. These substances, normally dispersed in the medium in the absence of bubbles, are thus assembled in the form of aggregates on the free surface of the gravity tank when the bubbles burst. The bacteria and fungi that would not be able to develop due to the strong dilution of these organic molecules then find concentrated substrates favorable to their development.

BRIEF SUMMARY

One of the aims of the present invention is to prevent, or at least limit, the formation of bubbles to:

contain bacterial and fungus development, for example to remain compatible with the health standards traditionally imposed in microorganism growth; and to limit mechanical stresses in the liquid culture medium, and thereby allow the growth of certain fragile microorganisms that were, until then, excluded from such growth in reactors.

In one alternative embodiment of the gas-lift, the deoxygenation of the liquid culture medium circulating in the photobioreactor is obtained by causing the liquid medium to drop gravitationally in a container with a constant level. The liquid culture medium is here made to circulate by a pumping means, in particular of the centrifugal pump type, positioned in the reaction channel designed not only to offset the energy losses in the channel, but also to raise the culture from the height of the drop.

Although it does not generate as many bubbles, this device with a centrifugal pump is as mechanically damaging for microorganisms as the gas-lift. Indeed, to overcome the energy losses, upon each passage at the pumping means, mechanical stresses are created that can hinder the growth of the microorganisms and cause mortalities within the culture. The production performance is thus altered, sometimes cripplingly.

For example, it has been observed that it is not possible to grow certain so-called fragile microalgae in photobioreactors including centrifugal pumps to make the culture circulate. These fragile microalgae appear to be even more sensitive to mechanical stresses when they form chains and/or have appendices such as silks, flagellae, and spicules. Certain microalgae, such as for example algae of the *Haematococcus pluvialis* type, lose their flagellae and become encysted in the form of a thick and resistant cellular wall. However, other microalgae, such as for example algae of the *Chlorella vulgaris* or *Nannochloropsis oculata* type, do not have appendages and have a thick cellular wall, such that they resist the passage in the pumping means, and in particular in the centrifugal pumps.

It is, however, difficult to identify the nature of the mechanical stresses influencing the survival and growth of the microorganisms. Most authors are in agreement that shear stress and accelerations have the most deleterious influence. Shear stresses create tensions that can alter the cellular integrity with tearing of the wall of the microorganisms and bleeding of the cytosol. Accelerations alter the cell structure by increasing the gravitational field.

Living cells are poorly prepared for these stresses, and this may be even more true for aquatic cells that live in hydrostatic equilibrium and have not developed a structure capable of overcoming a gravitational field. Moreover, aquatic cells are sensitive to threshold values and probably also to variations and exposure times. With the knowledge currently available, it is difficult to predict the mechanical effects of the hydrodynamic conditions imposed on the cells.

The invention is intended to reduce the mechanical stresses imposed on the microorganisms, in particular the effects of the shear stress and acceleration type, in order to extend the number of species that can be cultivated inside the reactor to those most sensitive to these harmful mechanical effects, in other words to offer a reactor making it possible to grow fragile microorganisms, such as, for example, the fragile microorganisms cited above.

Moreover, the applicant has observed that the growth yield of photobioreactors equipped with gas-lifts or centrifugal pumps was limited in particular due to the formation of bubbles. Indeed, the applicant has established that the growth yield depends in part on the phenomena involved in the gas-liquid transfer to avoid losses and reduce this significant expenditure. Modeling the gas-liquid transfer of the carbon dioxide intended for the reaction and the oxygen it produces requires determining the transfer speed, which depends on the surface transfer coefficient.

The surface transfer coefficient is a key parameter that translates the performance of a gas/liquid exchange in the stable state. This surface transfer coefficient is equal to the product of the mass transfer volume coefficient "KL" ($m \cdot s^{-1}$) and the interfacial area per unit volume "a" ($m^{-1}$), where:

$$a = (\alpha_G \cdot S)/V$$

a: Interfacial area per unit volume ($m^{-1}$);
$\alpha_G$: phase retention coefficient;
S: Contact surface; and
V: Volume of the reactor.

The surface transfer coefficient therefore depends on the geometry of the gas/liquid exchange system, but also the physico-chemical properties of the liquid and the gas. In the case of a gas/liquid exchange within a vertical bubble column, the exchange surface depends on the number of bubbles and their size. The bubble population created by a gas injection in a liquid depends on the rate of injection, the geometry of the injector, and the pressure difference on either side thereof.

The present invention aims in particular to provide a photosynthetic reactor that allow mass cultivation of photosynthetic microorganisms, and its extension to the most fragile species, with a reactor that resolves the following issues:

reducing, or even eliminating the mechanical stresses generally related to agitating and circulating the culture medium and that decrease the survival and growth performance of the photosynthetic microorganisms such as microalgae, and more particularly microalgae in chains provided with appendages;

reducing, or even avoiding the production of small bubbles likely to favor the aggregation of the organic molecules and development of the heterotrophic microorganisms for which it serves as substrate;

all while carrying out the photonic transfer, to deliver the solar radiation to the photosynthetic microorganisms, the mass transfer or gas/liquid transfer essential to provide carbon and evacuate oxygen, and the heat transfer, to evacuate the calories provided by the radiation and keep the culture at the right temperature; and all while maintaining mechanical conditions preserving the integrity of the cells and preventing exchanges with the surrounding medium of a nature to lend itself to contamination and dissemination.

The greatest limitation of the three embodiments described above in the development of algae production comes from the fact that they are intended for submerged surfaces of the planet, which are used as a priority for urbanization and food crops, and their rarity increases with human demographics. This lack of surface severely limits the development by these means of microalgae cultures, in particular for energy purposes, that should, to play a significant role, occupy considerable surfaces.

To respond to this issue, the production of algae cultures was considered in desert regions, but this prospect is thwarted by the low availability of water to produce the reaction liquid medium and for its cooling by evaporation.

Yet the expanses of water, such as for example natural and artificial water surfaces of the continents and especially the seas, cover the majority of the surfaces of the Earth and are still only slightly developed for their exposure to the light. These expanses of water or aquatic surfaces are naturally the seat of considerable plant productions that constitute the first level of aquatic trophic chains exploited in part by world fisheries. The primary production of the oceans, currently estimated at about $10^{11}$ tons per year, is the most significant on the planet. The plant masses are consumed by herbivores as soon as they are produced, which makes them not very visible, and makes them sporadic, diluted, and difficult to separate from the ambient water mass, and never pure. This explains why this abundant resource is not directly exploited for humans.

One of the aims of the invention is to propose a reaction jacket, for a photosynthetic reactor, adapted to grow photosynthetic microorganisms, able to be deployed on an expanse of water or on the surface of water and sea planes. To that end, the invention proposes to use these expanses of water receiving solar radiation to carry out, aside from the water resource, two essential functions of photobioreactors, i.e. horizontal surface lift and thermal stability.

Known, in the prior art, are several types of photosynthetic reactors deployed on an expanse of water in order to respond to this issue of the use of expanses of water.

It is thus known, from patent application FR 2 621 323, to provide a photobioreactor including a reaction jacket made in the form of a first set of parallel tubes, made of flexible plastic material, such as polyethylene, connected to each other at their two ends using two respective upstream and downstream collectors. This first set of tubes ensures the confinement of the liquid culture medium. The photobioreactor also comprises a second set of tubes placed below the first set of tubes, where the tubes of this second set are intended to be inflated with compressed air to form a floating pneumatic support. Such a photobioreactor has a number of drawbacks, the main ones being: a complex and costly reaction jacket with a succession of upstream and downstream tubes and collectors makes the reaction jacket heavier, and a complex structure intended to ensure the flotation of the reaction jacket on the expanse of water imposed in particular by the presence of these collectors.

Documents FR 2 361 060 and FR 2 324 224 respectively describe a photosynthetic reactor including a reaction jacket made in the form of a series of transparent tubes connected to each other to define a winding continuous flow path, for the liquid culture medium. These tubes are housed to form a floating structure including float containers. Such a reactor has a number of drawbacks, the main ones being: a complex and costly reaction jacket with a succession of tubes connected to each other at their ends, these tubes requiring a complex structure intended to ensure the floating of the assembly.

Document WO 2009/051479 A2 describes a photobioreactor including a reaction jacket made in the form of a series of transparent tubes connected to each other by coupling parts to define a winding continuous flow path, for the liquid culture medium. To ensure the floatation of these tubes, the photobioreactor comprises floats attached on the tubes. Such a photobioreactor has a number of drawbacks, the main ones being: a complex and costly reaction jacket with a succession of tubes connected to each other at their ends by coupling parts, these tubes requiring the addition of floats intended to ensure the floatation of the assembly.

Document WO 2008/134010 A2 describes a photobioreactor provided with a reaction jacket made in the form of a tube made of a flexible and transparent material carrying out the confinement of the liquid and gaseous volumes, and floats positioned on the sides of the tube to ensure the floatation of the assembly. The deployment of the confinement volume is obtained using stiffeners and cross-pieces and the gas/liquid diphasic circulation occurs in a single direction. In this photobioreactor, the tube must be connected at both ends to other installations ensuring the setting in motion and closing of the reaction liquid loop.

Document WO 2009/090549 A2 describes a photobioreactor provided with a reaction jacket made in the form of a tubular slug in a flexible and transparent material. In this photobioreactor, the gas contribution ($CO_2$) to the liquid culture medium can be done by passive gas diffusion on a wide area of the liquid medium, by injection of gas bubbles, in particular in the lower portion of the reaction slug, with all of the aforementioned drawbacks relative to the production of bubbles.

The reactors described in the aforementioned documents FR 2 621 323, FR 2 361 060, FR 2 324 224, WO 2009/051479 A2, WO 2008/134010 A2 and WO 2009/090549 A2 also have an additional shared drawback: the cleaning of the reaction jacket, inside and outside, is particularly complex, and requires at least partial disassembly of the jacket, knowing that the development of soiling or biofilms on the inner or outer walls of the reaction jacket is harmful to the transparency of the reaction jacket and therefore the production yield of photosynthetic organisms.

In order to respond to all or part of the drawbacks and issues raised above, the present invention proposes, to that end, a reaction jacket for a photosynthetic reactor adapted for growing photosynthetic microorganisms, in particular algae, said reaction jacket being designed, on one hand, to float on an expanse of water and, on the other hand, to define a gas/liquid culture medium diphasic flow path between first and second openings of said reaction jacket, said reaction jacket being remarkable in that it includes two sheaths, outer and inner, respectively, made at least partially from a material transparent to light radiation, the inner sheath extending to the inside of the outer sheath such that said sheaths define an inter-sheath space between them in fluid connection with the first opening of the reaction jacket, in that the outer sheath has an open proximal end and a closed distal end, and in that the inner sheath has an open proximal end in fluid connection with the second opening of the reaction jacket and a distal end provided with at least one communication orifice between the inside of the inner sheath and the inter-sheath space.

With this jacket, the diphasic flow path is done, between the first opening and the second opening, in the inter-sheath space and inside the inner sheath via the communication orifice formed at the distal end of the inner sheath.

Thus, this jacket allows the production of photosynthetic microorganisms, in particular microalgae, by monoclonal growth under controlled conditions, that can be deployed on the surface of an expanse of water (water plane or sea). This jacket should thus contribute to the development of those expanses of water that have the most abundant surfaces and are the least developed on the planet, to produce photosynthetic microorganisms.

In fact, this jacket proposes to exploit several intrinsic features of the expanses of water, i.e.:

the thermal inertia related to the significant heat capacity of the water which, through the exchange with the culture medium through the outer sheath, makes it possible to keep the temperature at levels close to optimum for the cultivated photosynthetic microorganisms, the lift capacity of the bodies having a lower density than the water that makes it possible to ensure the hydrostatic maintenance of the surface culture volume according to the natural horizontal of the water planes, thereby avoiding gravitational flows and the formation of unwanted bubbles; and the transparency of the expanses of water, when they do not receive loam.

The expanse of water can serve as local water source for the culture, but it is desirable to treat it so as to remove the unwanted microorganisms from it, as well as certain substances such as excess minerals.

The present invention is applicable to growing any photosynthetic organism, i.e. any life form likely to develop through photosynthesis in a suitable nutritional culture medium, in the presence of solar radiation and carbon, in particular in the form of carbon dioxide.

This reaction jacket, adapted to the expanses of water, makes it possible to carry out the following functions:

ensure, over time, the confinement of the culture by preventing exchanges of mass with the surrounding medium that lends itself to contamination and dissemination, and to that end to resist mechanical stresses in particular by currents, wind, and surface agitation;

ensure the photonic transfer to deliver solar radiation to the microorganisms in the culture;

ensure the gas/liquid mass transfer essential to provide carbon and evacuate oxygen from the reaction;

ensure the heat transfer, to evacuate the calories contributed by the radiation and keep the culture at the right temperature;

lend itself to a decrease of costs of the biomass produced by a moderate cost of the means implemented in said jacket.

The jacket according to the invention makes it possible to obtain these results, and to that end has a particular confinement, with two sheaths one in the other defining a continuous flow path of the liquid and gas reaction mediums, which lends itself to scaling up towards large surfaces; the plant production of the photosynthetic microorganism production systems being, in fact, proportional to said surface according to a factor called surface productivity, the value of which is in the vicinity of several tens of grams of dry matter per square meter and per day.

Advantageously, at least one of the two sheaths, outer and inner, respectively, is made from a flexible material adapted to allow the folding, inflation, transverse deformation and/or bending of said sheath. Preferably, the two sheaths are made in such a flexible material.

Flexible material refers to a material that can be deformed, folded, wound, bent without tearing or breaking, such as a supple or ductile material. Such a material is particularly adapted for the jacket according to the invention because it makes it possible for:

the jacket in its entirety to be folded or wound in order to be stored in a folded or wound form, before being deployed on the expanse of water by inflation, such an inflation being done by filling using gas and/or liquid before establishing their round-trip circulation;

the inner sheath deforms and bends inside the outer sheath, such that the outer wall of the inner sheath rubs against the inner wall of the outer sheath, thereby cleaning this inner wall of the outer sheath and this outer wall of the inner sheath;

the outer sheath deforms and bends, such that the inner wall of the outer sheath rubs against the outer wall of the inner sheath, thereby cleaning this outer wall of the inner sheath and this inner wall of the outer sheath, and such that the outer sheath rubs against an outer sheath of a neighboring or adjacent reaction jacket, thereby cleaning the outer walls of these two outer sheaths;

the manufacturing costs of these jackets are reduced with the use of a relatively economical flexible material.

In one particular embodiment, the jacket also comprises:

an outer connecting piece on which the proximal end of the outer sheath is hermetically mounted, and on which the first opening of the reaction jacket is formed in fluid connection with the inter-sheath space; and an inner connecting piece on which the proximal end of the inner sheath is hermetically mounted, and on which the second opening of the reaction jacket is formed in fluid connection with the proximal end of the inner sheath.

These connecting pieces, for example assuming the form of plates, are particularly advantageous to make the hermetic or sealed connection of the two sheaths with a closing channel providing the outer fluid connection at the jacket between the first and second openings of the reaction jacket. Moreover, these connecting pieces make it possible to pick up the longitudinal stresses transmitted by the sheaths, and especially by the outer sheath, to transmit them to a craft supporting the closing channel in which a means is providing for making the liquid medium circulate.

According to one feature, the proximal end of the inner sheath is rotatably mounted on the inner connecting piece, such that the inner sheath is free to rotate and oscillate inside the outer sheath, thereby favoring the cleaning of the walls.

According to another feature, the inner connecting piece is mounted inside the outer connecting piece, thereby limiting the bulk of the connecting pieces with the proximal ends of the sheaths situated substantially in the same plane defined by the two pieces.

Advantageously, the outer connecting piece includes means for coupling with means for driving said outer connecting piece in rotation so as to drive the outer sheath in rotation. This driving in rotation of the outer sheath is particularly advantageous to clean the outer wall of the outer sheath.

Preferably, the inner connecting piece freely rotates in the outer connecting piece, so that the rotation of the outer sheath ensures the rotation of the inner sheath by friction between the two sheaths. The rotation of the outer sheath is thus communicated to the inner sheath, favoring the movements of the sheaths and therefore the cleaning of their walls.

In one particular embodiment, the inner sheath, shorter than the outer sheath, extends over at least 90% of the length of the outer sheath, preferably over the entire length of the outer sheath decreased by its diameter, so as to optimize the gas/liquid diphasic flow length and therefore the exchanges between the two phases.

According to one possibility of the invention, the communication orifice, provided on the distal end of the inner sheath, has a convergence area, in order to produce an energy loss of the gas/liquid culture medium diphasic flow, and therefore create an excess pressure that ensures the inflation of the inner sheath over its entire length.

This convergence area is for example made in the form of a reduction of the diameter of the inner sheath at the open distal end thereof.

According to another possibility of the invention, the jacket also includes a third sheath in a flexible material extending inside the inner sheath so as to allow an injection or suction of gas at the distal ends of the two sheaths, inner and outer, respectively.

In the case of a gas injection in this third sheath, the gas return is done via the inter-sheath space, whereas in the case of a gas suction in this third sheath, the outward journey of the gas is done via the inner sheath and/or the inter-sheath space. This last configuration is particularly adapted to agitated or wavy planes of water where the undulation of the surface will tend to move the injected gas towards the distal end of the two sheaths, outer and inner, respectively.

In one particular embodiment, the jacket also comprises:

removable clipping or binding means designed to clip or bind the two sheaths on an intermediate area situated between the respective proximal and distal ends of the two sheaths;

at least one intermediate communication orifice between the inside of the inner sheath and the inter-sheath space, said intermediate communication orifice being provided on the inner sheath between its proximal end and said intermediate clipping or binding area; and means for closing said intermediate communication orifice, in particular of the flap type, said closing means being able to move between an open position and a closed position.

In this particular embodiment, it is possible to exploit only a reaction sub-volume, corresponding to the portion of the jacket between the proximal ends of the sheaths and the intermediate clipping or binding area, in order to inoculate and culture this sub-volume, before culturing the entire volume by removing the clipping or binding means and closing the closing means of the intermediate communication orifice.

The invention also concerns a photosynthetic reactor adapted for growing photosynthetic microorganisms, in particular algae, including:

at least one reaction jacket according to the invention;

at least one closing channel ensuring the fluid connection between the first and second openings of said reaction jacket;

at least one circulation means positioned in said closing channel and designed to make the liquid culture medium circulate in the closing channel and in the reaction jacket;

at least one means for injecting liquid positioned in said closing channel and designed to make it possible to inject liquid into the reaction jacket;

at least one means for injecting gas positioned in said closing channel and designed to make it possible to inject gas into the reaction jacket; and at least one gas exhaust means positioned in said closing channel and designed to make it possible to allow gas injected into the reaction jacket to escape.

This reactor can of course include several reaction jackets with a circulation means shared by all of said jackets.

With a reactor according to the invention, the liquid culture medium and the gas circulate at the same time in contact with each other along the substantially horizontal diphasic flow path because the reaction jacket, and therefore the sheaths defining said path, float on the surface of the water, which is primarily horizontal (with allowance for variations caused by the wind, waves, surface movements, etc.), and exchange certain components along their shared paths. The exchanges between the liquid culture medium and the gas are proportional to the length of the sheaths, which makes it possible consider large scaling up.

The reactor and the reaction jacket according to the invention are thus specially designed to increase the effectiveness of the gas-liquid transfer and to decrease the mechanical stresses inflicted on the cultured organisms in order to extend the production of fragile species.

Moreover, the reactor and the reaction jacket according to the invention make it possible to limit the formation of bubbles with small diameters and thereby to reduce the development of heterotrophic microorganisms consuming oxygen. Indeed, with the reaction jacket according to the invention, the gas/liquid transfer no longer takes place inside a vertical column of bubbles, but along a substantially horizontal flow path in which the flow follows a regime of the horizontal diphasic type, in particular of the stratified flow type or flow type with slugs or elongated bubbles.

Contrary to the aforementioned principle according to which the reaction only takes place in the liquid phase, the applicant started from the principle that the gas is an integral part of the reaction and must be allowed in the reaction volume just like the liquid. By favoring horizontal diphasic flow regimes (stratified, with slugs or with elongated bubbles), the exchange surface between the gas and the liquid is extended to the entirety of the path in the reaction jacket with a bubble production that is markedly less abundant than in the case of certain reactors of the prior art, thereby reducing the deleterious effect observed for those bubbles.

Moreover, in the reactor according to the invention, the circulation of the liquid culture medium is done by one or several circulation means creating reduced shear stress and centrifugal forces. The circulation function is dissociated from the gas-liquid exchange function, unlike the case of reactors with a gas lift.

The invention also concerns a method for growing photosynthetic microorganisms, in particular algae, using a reactor according to the invention and comprising the following steps:

injecting a liquid culture medium into the reaction jacket at a rate controlled with the liquid injection means;

injecting a gas into the reaction jacket at a rate controlled with the gas injection means;

circulation of the liquid culture medium with the circulation means;

control of the circulation means and the gas injection means to establish, in the reaction jacket, a gas/liquid culture medium diphasic flow regime of the stratified flow or flow with slugs or with elongated bubbles type.

According to one feature, the control step comprises a step for controlling the circulation speed of the liquid in the reaction jacket between about 0.1 and 1.0 m/s.

According to another feature, the circulation means comprises a propeller driven in rotation by a motor, and the rotational speed of the propeller is less than about 1000 rpm, preferably less than about 100 rpm.

According to one feature, the injection of the liquid culture medium and gas into the reaction jacket is done to inflate and deploy the jacket on the surface of the expanse of water.

The invention also concerns a method for making a reaction jacket according to the invention, comprising the following steps:

making the inner sheath, in particular by an extrusion method of a plastic material and inflating the extruded plastic;

making an outer sheet in a plastic material, in particular by a calendering method;

surrounding the inner sheath with the outer sheet up to a junction of two opposite edges; and welding the outer sheet along its two opposite edges joined during the surrounding step, so as to form the outer sheath surrounding the inner sheath.

These steps can be completed by a winding or folding step of the inner and outer sheaths thus made.

The production method according to the invention is particularly economical and rapid.

BRIEF DESCRIPTION OF THE DRAWINGS

Other features and advantages of the present invention will appear upon reading the detailed description that follows, of several non-limiting embodiments, done in reference to the appended figures, in which:

FIG. 1 is a transverse cross-sectional diagrammatic view of a jacket according to the invention;

FIG. 2a is a back diagrammatic view of a jacket according to the invention, illustrating a connecting piece shared by the sheaths of the jacket;

FIG. 2b is a partial longitudinal cross-sectional view along axis II-II of the jacket illustrated in FIG. 2a, illustrating the proximal ends of the sheaths;

FIG. 6b is a transverse cross-sectional view along axis VI-VI of the right part of the reactor illustrated in FIG. 6a;

FIG. 7a is a partial diagrammatic profile view of a reactor according to the invention comprising a closing channel integrating means for making the liquid medium circulate according to a second embodiment;

FIG. 7b is a transverse cross-sectional view along axis VII-VII of the right part of the reactor illustrated in FIG. 7a;

FIG. 7c is a transverse cross-sectional view along axis VII-VII of the left part of the reactor illustrated in FIG. 7a;

FIG. 7d is a top view of the reactor illustrated in FIG. 7a;

FIG. 8a is a partial diagrammatic profile view of a reactor according to the invention comprising a closing channel integrating means for making the liquid medium circulate according to a third embodiment;

FIG. 8b is a back view of the reactor illustrated in FIG. 8a;

FIG. 9a is a partial diagrammatic profile view of a reactor according to the invention comprising a closing channel integrating means for making the liquid medium circulate according to a fourth embodiment;

FIG. 9b is a back view of the reactor illustrated in FIG. 9a;

FIG. 12b is a partial diagrammatic top view of the two reactors illustrated in FIG. 12a;

FIG. 13b is a longitudinal cross-sectional view along axis XIII-XIII of the reactor illustrated in FIG. 13a;

DETAILED DESCRIPTION

Figure 3A:
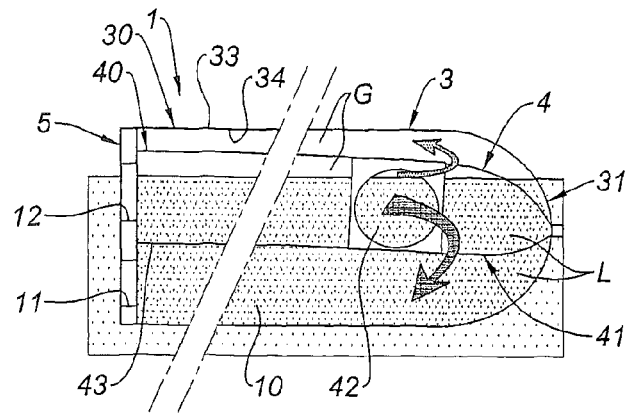
FIGS. 3a and 3b are diagrammatic longitudinal cross-sectional views of two jackets according to the invention, illustrating two embodiments of a communication orifice provided at the distal end of the inner sheath.

The description of a reaction jacket according to the invention for a photosynthetic reactor 2, or photobioreactor is done in reference to FIGS. 1 to 3; this jacket 1 being adapted for the growth of photosynthetic microorganisms, in particular algae, and in particular for the growth of photosynthetic organisms fragile to mechanical stresses.

The jacket 1 is designed, on one hand, to float on an expanse of water and, on the other hand, to define a gas/liquid culture medium diphasic flow path between first 11 and second 12 openings of the reaction jacket 1. To that end, the jacket 1 includes:

an outer sheath 3 at least partially made of a flexible material transparent to light radiation, where the outer sheath 3 is elongated, in particular with a general tubular shape, and has an open proximal end 30 and a closed distal end 31, in other words ending in a cul-de-sac;

an inner sheath 4 at least partially made of a flexible material transparent to light radiation, where the outer sheath 3 is elongated, in particular with a general tubular shape, extends inside the outer sheath 3 such that these two sheaths 3, 4 define an inter-sheath space 10 between them, and has an open proximal end 40 and a distal end 41 provided with at least one communication orifice 42 between the inside of the inner sheath 4 and the inter-sheath space 10;

an outer connecting piece 50 on which the proximal end 30 of the outer sheath 3 is hermetically mounted, and on which the first opening 11 of the reaction jacket 1 is formed in fluid connection with the inter-sheath space 10; and an inner connecting piece 51 on which the proximal end 40 of the inner sheath 4 is hermetically mounted, and on which the second opening 12 of the reaction jacket 1 is formed in fluid connection with the proximal end 40 of the inner sheath 4.

The outer sheath 3 has a length of several tens of meters and a decimetric diameter, for example between about 5 and 50 cm.

The inner sheath 4 has:

a length substantially equivalent to that of the outer sheath 3, for example a length greater than about 90% of the length of the outer sheath 3 and preferably equal to the length of the outer sheath 3 decreased by its diameter; and a diameter substantially smaller than that of the outer sheath 3.

The inner sheath 4 is thus deployed in the outer sheath 3 freely and over about all of its length.

The two sheaths 3, 4 are made of a flexible material, in other words in a material adapted to allow the folding, inflation, transverse deformation and/or bending of the sheaths 3, 4.

Concerning the resistance of the sheaths 3, 4, the membrane of the outer sheath 3 must be able to resist the tractive force related to the movement of the mass of the expanse of water, that of the air being negligible. This force is substantially equivalent to the drag force of a boat of the same length on a wet surface for a same relative speed. This approach to calculating the tractive forces to which the sheaths 3, 4 are subjected, and which are transmitted to a mooring support (floating craft E described later, dock or bank) via connecting pieces 50, 51, is, however, lower bound because it neglects surges. A safety margin must be taken, knowing that only the outer sheath 3 picks up these forces.

The Applicant has thus established a list of plastic materials that can be used to make the sheaths 3, 4, including in particular polyethylene, polypropylene, polyamides (Nylon, Rylsan), polytetrafluorethylenes (PTFE), either in membrane form, or in woven fiber form, or in a composite form of calendered or coated fabrics. This list is of course not limiting and can in particular be completed by new transparent materials appearing on the market.

The membranes or films made of these plastic materials have tensile strengths of several tens of kilograms per linear meter, which is in the vicinity of a hawser or rope used in marine applications with a small diameter. With such materials, the outer sheath 3 can therefore resist the tractive forces caused by the wind. It is therefore advantageous to ensure that the mooring support, such as the floating craft, transmits as little surge as possible to the jacket 1 and its sheaths 3, 4.

As illustrated in FIGS. 2a and 2b, the inner connecting piece 51 is mounted inside the outer connecting piece 50, such that these two connecting pieces 50, 51 together form a connecting or fastening plate 5, intended to allow the connection of the sheaths 3, 4 with a closing channel 7 described later.

The outer connecting piece 50 includes means 52 for coupling with means 53 for driving said outer connecting piece 50 in rotation so as to drive the outer sheath in rotation 3. Thus, the proximal end 30 of the outer sheath 3 is hermetically associated with a rotary fastener, i.e. the outer connecting piece 50. The rotational speed implemented by the driving means 53 is in the vicinity of a few revolutions per day.

In the embodiment illustrated in FIGS. 2a and 2b, the coupling means 52 is made in the form of a pulley formed on the cylindrical periphery of the outer connecting piece 50, and the driving means 53 comprises a rotary engine provided with an rotating output shaft 530 on which a belt or a chain 531 is mounted meshing on the pulley 52.

The inner connecting piece 51, included in the connecting plate 5, freely rotates in the outer connecting piece 50, so that the rotation of the outer sheath 3 by the driving means 53 ensures the rotation of the inner sheath 4 by friction between the two sheaths 3, 4. Thus, the proximal end 40 of the inner sheath 4 is rotatably mounted on the plate 5. In other words, the proximal end 40 of the outer sheath 4 is hermetically associated with a rotary fastener, i.e. the outer connecting piece 51.

The connecting plate 5 is intended to pick up the longitudinal tensile forces transmitted by the sheaths 3, 4, and especially the outer sheath 3, to transmit them to the mooring craft E.

This connecting plate 5 is partially submerged in the expanse of water and is animated by a uniform or alternating rotational movement, such that it ensures:

the setting in rotation, or oscillation, of the sheaths 3, 4 with an angular amplitude greater than or equal to 360°, or over at least one complete revolution, this rotation being illustrated by the arrow R1 in FIGS. 1 and 2a;

the free rotation of the inner sheath 4 inside the outer sheath 3, this rotation being illustrated by the arrow R2 in FIGS. 1 and 2a; and the maintenance of the integrity/sealing of the confinement done by the jacket 1, while hermetically allowing these rotational movements.

To achieve this hermetic fastening and therefore avoid leaks, a joint 54 equipped with an anti-friction and sealing device is provided between the connecting plate 5 fastener and the outer sheath 3; the inner volume of the jacket 1 being pressurized, any leaks will go towards the outside, which limits the risk of contamination. A joint 55 equipped with an anti-friction and sealing device is also provided between the connecting plate 5 fastener and the inner sheath 4, although the consequences of any leak at that level are not serious.

To decrease the rotational driving force of the connecting plate 5, the plate 5 is provided with ball bearings 56 below the pulley 52.

The rotation of the outer sheath 3 is communicated to the inner sheath 4, the inner connecting piece 51 of which is freely rotating as described above in the plate 5, by their friction.

As visible in FIGS. 2a and 2b, the fastening of the inner sheath 4 on the plate 5 is slightly upwardly offset to:

allow an installation of the gas outlet, also called the gas exhaust means 60, in the upper portion; and also to favor contact between the two sheaths 3, 4, this contact ensuring the rotational driving, or oscillating driving, of the inner sheath 4 by the outer sheath 3.

Opportunely and as visible in FIG. 2b, the orifice of the gas exhaust means 60, i.e. of the gas outlet, is equipped with a float closure 600 intended to prevent the passage of the liquid.

Figure 3B:
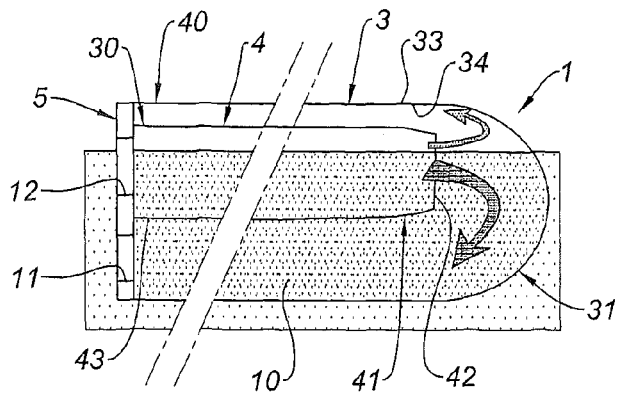

FIGS. 3a and 3b illustrate two jackets with two distinct embodiments of the communication orifice 42. In the embodiment illustrated in FIG. 3a, the communication orifice 42 is formed on the lateral wall of the inner sheath 4, in the form of a window that may be provided with reinforcements on its edges, where the distal end 41 of the inner sheath 4 is integrally fastened, in particular by welding or by a shared clipping or binding, to the distal end 31 of the outer sheath 3. In the embodiment illustrated in FIG. 3b, the communication orifice 42 is arranged at the end of the distal end 41 of the inner sheath 4, such that it is an open and free distal end 41.

The cleaning of the transparent walls of the sheaths 3, 4 is one of the main advantages of the jacket 1 according to the invention. Indeed, this cleaning aims to prevent the development of biofilms on their respective walls, so as to avoid a decrease in the light transmitted that is harmful because it slows the reaction.

To perform this cleaning, several functions are carried out:

the relative movements and the rubbing of the adjacent outer sheaths 3 against each other allows the cleaning of their respective outer walls 33, these relative movements being obtained in particular by deformation and bending of the flexible outer sheaths 3 under the action of the agitation of the expanse of water caused in particular by the wind (chop);

the rotation of the outer sheath 3 over at least one revolution (angular amplitude greater than or equal to 360°), makes it possible to extend the aforementioned cleaning of their outer walls 33 to their entire periphery;

the relative movements between the two sheaths 3, 4 caused by the rotation of the outer sheath 3 associated with the action of the agitation of the expanse of water and the flexibility of their materials leads to the rubbing of the inner sheath 4 against the outer sheath 3, which allows the cleaning of the inner wall 34 of the outer sheath 3 and the cleaning of the outer walls 43 of the inner sheath 4;

the rotation of the outer sheath 3 over at least one revolution (angular amplitude greater than or equal to 360°) makes it possible to extend the aforementioned cleaning of the inner walls 34 of the outer sheath 3 and the cleaning of the outer walls 43 of the inner sheath 4 to their entire periphery.

Thus, the contact between the two sheaths 3, 4 of a same jacket 1 results in preventing the development of a biofilm and ensures the cleaning both of the inner wall 34 of the outer sheath 3 and the outer wall 43 of the inner sheath 4. The rotation, or an oscillation, with an angular amplitude greater than or equal to 360°, aims to ensure that this cleaning is done on the entire periphery of the sheaths.

As illustrated in particular in FIGS. 1 and 3, the liquid culture medium L and the gas G circulate at the same time in contact with each other and exchange matter through a gas-liquid interface along the reaction path going from the inside of the inner sheath 4 to the inter-sheath space 10, or conversely. The shape of this inter-sheath space 10 depends in particular on the relative position of the two sheaths 3, 4 and the flow regime, itself depending on the gas and liquid flows.

As illustrated in particular in FIGS. 1 and 3, the density of the matter making up the sheaths 3, 4 not being very different from that of the water, the average levels of the gas-liquid interface in the inter-sheath space 10 and in the inner sheath 4 are substantially identical to that of the water plane; these levels determining the inner and outer waterlines.

As shown in FIG. 1, the contact zone ZC between the inner sheath 4 and the outer sheath 3 is situated above the waterline. It results from this that the inter-sheath space 10 has an asymmetrical section in closed crescent shape, as indicated by FIG. 1. The inner sheath 4 tends to remain in contact with the outer sheath 3 by the capillary force exerted by the liquid film in the contact zone ZC between the two sheaths 3, 4 in the inter-sheath space 10. The liquid film of the contact zone ZC, the thickness of which is small, is maintained by capillarity from the liquid culture medium L circulating in the inter-sheath space 10.

The connecting or contact force between the two sheaths 3, 4 is weak and the contact can be locally and temporarily undone by the movements of the water plane and the deformations of the sheaths 3, 4 that it causes. The weakness of the contact and the movements of the water plane in particular cause the contact to be accompanied by sliding and friction that prevent the development of a biofilm and favor the cleaning of the walls 43 and 34 involved in the contact, i.e. the inner wall 34 of the outer sheath 3 and the cleaning of the outer walls 43 of the inner sheath 4.

As described above, the rotation of the outer sheath 3 is transmitted to the inner sheath 4 by the friction in the contact zone ZC, despite the sliding that alters the quality of the driving. A certain stiffness of the inner sheath 4 is necessary to prevent it from folding and to generalize the cleaning effect on the walls 43 and 34. To avoid the consolidation of the biofilm between two contacts, it is enough for example for the speed of rotation to be less than a day, as suggested above.

The two sheaths 3, 4 channel the path of the gases and liquids of the culture in a gas G/liquid culture medium L diphasic flow path (or reaction path), forming a round trip journey between the openings 11, 12 of the jacket 1, in the inner sheath 4 and in the inter-sheath space 10 separating the inner sheath 4 from the outer sheath 3.

The circulation of gas in the sheaths 3, 4 creates a positive buoyancy distributed homogeneously over the length of the sheaths 3, 4, which keeps them on the surface. The horizontal position is ensured naturally by the lift of the expanse of water and by the circulation of the gas. The agitation of the expanse of water under the effect of the wind can translate to longitudinal deformations of the outer sheath 3, which can be transmitted to the inner sheath 4, the flexibility or suppleness of the sheaths 3, 4 making it possible to recall or return to the initial shapes.

Preferably, it is necessary to prevent folds from appearing, with a substantial decrease of the reaction volume. Indeed, such folds could cause surges and other water hammers in case of agitation of the expanse of water, which would cause brutal tension of the flexible material of the sheaths 3, 4 capable of causing tearing of the sheaths 3, 4 in question. To that end, the outer sheath 3 must be continuously stretched owing to an excess inflation pressure; a control of this excess pressure making it possible to keep the outer sheath at a nominal level compatible with the agitation of the expanse of water and the proper operation of the assembly.

Thus, a photosynthetic microorganism culture method using such a jacket 1 comprises a step for pressurizing the outer sheath 3 comprising creating an excess inflation pressure in said outer sheath 3.

The excess inflation pressure of the outer sheath 3 determines, as described above, its stiffness, in other words its resistance to the deformation related to the agitation of the water plane, and the influence of the latter on the inner diphasic flow of gas G and liquid L, this excess pressure being equal to the sum of the injection pressures of the gas and of the liquid in the volume of the outer sheath 3.

The control of the excess inflation pressure also aims to detect leaks. The output of the surplus gaseous volume is done by the exhaust means 60 described above and provided with an orifice formed in the upper portion of the plate 5, as indicated in FIG. 2b. The gas is for example channeled to a filter that makes it possible to avoid the retro-contamination of the reactor before being released into the atmosphere or recycled. A control of the output flow of the gas can be done, using a means for controlling the gaseous flow 601, such as a needle valve, in order to adjust the height of the ceiling (level of the liquid or of the gas/liquid interface) in the sheaths 3, 4.

FIGS. 4 to 13 illustrate photosynthetic reactors 2 according to the invention and adapted to grow photosynthetic microorganisms, in particular algae. Each reactor 2 comprises:

at least one reaction jacket 1 according to the invention;

at least one closing channel 7 (visible in particular in FIGS. 6, 7, 8, 9, 12 and 13) ensuring the fluid connection between the first 11 and second 12 openings of the jacket 1, said openings 11, 12 being formed in the connecting plate 5 on which said closing channel 7 is sealably connected;

at least one circulation means 8 (shown in FIGS. 7c and 13a) positioned in the closing channel 7 and designed to make the liquid culture medium L circulate in the closing channel 7 and in the jacket 1;

at least one means 9 for injecting liquid positioned in said closing channel 7 and designed to make it possible to inject liquid L into the jacket 1;

at least one means 61 for injecting gas positioned in said closing channel 7 and designed to make it possible to inject gas G into the jacket 1; and at least one gas exhaust means 60 positioned in said closing channel and designed to make it possible to allow gas G injected into the jacket 1 to escape.

The reactor 2 can comprise two distinct liquid injection means 9 making it possible to inject the liquid culture medium and the inoculum, respectively, into the reactor 2. These injection means 9 assume the form of injection ports allowing a connection to a source with asepsis control.

The reactor 2 can comprise:

one or several sensors 91 positioned on the closing channel 7 and adapted to provide the necessary signals to control the reaction, in particular signals representative of physical, chemical, or biological parameters of the quality of the culture, such as the temperature, the pH, the dissolved oxygen level and the turbidity of the liquid medium, etc., these controls being used in particular to regulate the gas and liquid injections in the reactor 2;

means for controlling the sterility of the gaseous and liquid mediums entering and exiting the space confined by the reactor 2;

regulating loops intended to regulate the main nutrient availabilities of the culture, in particular, the admission of sterile medium by the dry matter concentration, the pH by the $CO_2$ injection.

The closing channel 7 ensures the closing of the fluid path loop between the first 11 and second 12 openings of the jacket 1. The closing channel 7 is made of a material that is not transparent to solar radiation and/or can be positioned sheltered from the light inside a closed site or a closed craft E as shown in particular in FIGS. 4 and 11.

The circulation means 8, inserted on the return channel(s) 7, serves to cause the liquid culture medium to circulate in the jacket 1. Preferably, the circulation means 8 is chosen to create reduced shear stress and centrifugal forces. It is, however, possible to use all types of pumping means, and in particular centrifugal pumps, without going beyond the scope of the invention.

Preferably, the circulation function is dissociated from the gas-liquid mass exchange function, which is performed through their interface in the sheaths 3, 4 of the jacket 1 and which is exerted over their entire length. However, one particular embodiment (not shown) of the reactor according to the invention can include the implementation of a gas-lift type solution, described above, which ensures both the pumping and the gas-liquid mass exchange, without going beyond the scope of the invention.

The reactor 2 is particularly advantageous by applying the principle that the gas is an integral part of the reaction and must be allowed in the reaction volume just like the liquid by implementing a horizontal diphasic flow in the sheaths 3, 4 of the jacket 1 floating on the expanse of water, these two flexible sheaths 3, 4 included one in the other creating a round-trip journey of the gas and the liquid.

With such a jacket 1, and therefore with such a reactor 2, four possible diphasic path configurations can be considered:

a first journey: cocurrent circulation with the liquid L and the gas G entering into the jacket 1 through the second opening 12 and exiting the jacket 1 through the first opening 11, such that the liquid L and the gas G perform an outbound journey in the inner sheath 4 and a return journey in the inter-sheath space 10;

a second path: cocurrent circulation with the liquid L and the gas G entering the jacket 1 through the first opening 11 and exiting the jacket 1 through the second opening 12, such that the liquid L and the gas G perform an outbound journey in the inter-sheath space 10 and a return journey in the inner sheath 4;

a third path: countercurrent circulation with the liquid L entering the jacket 1 through the second opening 12 and exiting the jacket 1 through the first opening 11 and with the gas G entering the jacket 1 through the first opening 11 and exiting the jacket 1 through the second opening 12, such that the liquid L performs an outbound journey in the inner sheath 4 and a return journey in the inter-sheath space 10 and the gas G performs an outbound journey in the inter-sheath space 10 and a return journey in the inner sheath 4; and a fourth path: countercurrent circulation with the liquid L entering the jacket 1 through the first opening 11 and exiting the jacket 1 through the second opening 12 and with the gas G entering the jacket 1 through the second opening 12 and exiting the jacket 1 through the first opening 11, such that the liquid L performs an outbound journey in the inter-sheath space 10 and a return journey in the inner sheath 4 and the gas G performs an outbound journey in the inner sheath 4 and a return journey in the inter-sheath space 10.

In the case of the first path, the gas G and the liquid culture medium L are injected into the inner sheath 4 at the second opening 12 formed in the plate 5 and escape from said inner sheath 4 via the communication orifice 42 provided at the distal end 41, then return to the plate 5 level in the inter-sheath space 10.

In the case of the fourth path, the gas G is injected into the inner sheath 4 while the liquid culture medium L is injected into the inter-sheath space 10, the return of the gas G being done in the inter-sheath space 10 and that of the liquid L in the inner sheath 4.

In all cases, the liquid L is picked up on the return by at least one pump situated in the return channel(s) 7 to be reintroduced into the same outbound path, while the gas G is either released into the atmosphere or recycled via the gas exhaust means 60.

Preferably, the communication orifice 42, provided on the distal end 41 of the inner sheath 4, has a convergence zone in order to achieve an energy loss in the gas/liquid culture medium diphasic flow. In the embodiment illustrated in FIG. 3b, the open distal end 41 of the inner sheath 4 has a reduced diameter to create this singular energy loss, the excess pressure created by this convergence or restriction zone ensuring the inflation of the inner sheath 4 over its entire length.

Possibly, a third sheath (not illustrated), also made of a flexible material transparent to light radiation, with a stiff enough wall to be able to undergo a depression without collapse and with a small diameter (compared to the diameter of the inner sheath 4), is situated inside the inner sheath 4 to allow an injection or suction of gas at the distal end 31, 41 of the two sheaths 3, 4.

As visible in FIG. 1, the circulation of the gas G and of the liquid L, whether countercurrent or cocurrent, occurs along a substantially rectilinear horizontal path where the gas G gathers in a volume situated in the upper portion or top of the cavity defined by the two sheaths 3, 4.

An interface is thus created between the gas G and the liquid L that is the seat of the transfers related to the photosynthesis reaction. The longitudinal shape of that interface, and in particular its continuous or discontinuous nature, characterizes what is called the state of flow. Without considering the influence of the agitation of the water plane, the states of flow in the inner sheath 4 are substantially the same as in a horizontal channel with a circular section. These flows have been described using the names stratified or slug or elongated bubbles flow. The states of flow in the inter-sheath space 10 are slightly disrupted by the presence of the inner sheath 4, but will have substantially identical characteristics regarding the mass transfer.

Concerning the diphasic flows in horizontal ducts, work has shown several states of flow depending on the speed, diameter, temperature, nature, and circulating fluid pressure conditions, in particular:

dispersed bubbles flow, Mandhane AD typology; and
elongated bubbles flow, Mandhane I typology;
stratified flow, with a wavy stratified flow and a smooth stratified flow, Mandhane SS and SW typology;
slug flow, Mandhane I typology;
annular mist flow, Mandhane AD typology.

In the case of the present invention, the privileged states of flow are therefore situated at the SS/I transition in the Mandhane typology, i.e. between the stratified state and the slug or elongated bubbles state. In the stratified state, the gas/liquid interface is formed by the free surface, the width of which varies with the level of the liquid in the sheaths 3, 4. In the slug or elongated bubbles state, the gas/liquid interface is formed by the floor and the ceiling of the slug or of the elongated bubble.

The mass transfers being proportional to the length of the path, the effect thereof on the performance of the reaction is reduced, which makes it possible to consider large scaling up. The sheaths 3, 4 can have lengths of several hundreds of meters.

In the particular case of the first path described above, the gas G and the liquid L are injected simultaneously in the inner sheath 4. In order to avoid the reflux of the gas G countercurrent from the liquid L, the gas G is preferably injected at an injection point 61 situated downstream of a low point of the ceiling of the closing channel 7 that will serve as an anti-return, as illustrated in FIGS. 6, 7, 8 and 9. The separation of the liquid L and the gas G is completed by the positioning of the first opening 11, forming the outlet of the inter-sheath space 10, in the low portion of the plate 5. This separation is essential to not alter the performance of the circulation means 8.

The outlet of the excess liquid volume L in the reactor is done in particular by a spillway formed by an outlet channel 90 (visible in FIGS. 6a, 7a, 8, 9 and 12) communicating with the closing channel 7. The free end of this closing channel 90 is set at a height H that can be adjusted in relation to the water plane, this height H, visible in FIGS. 6a and 7a, determining the excess inflation pressure of the outer sheath 3 and being able to be adjusted to stabilize the inner flow as a function of the agitation of the water plane. This height H is in the vicinity of a few centimeters and can exceed several decimeters for very long sheaths 3, 4.

Figure 6A:
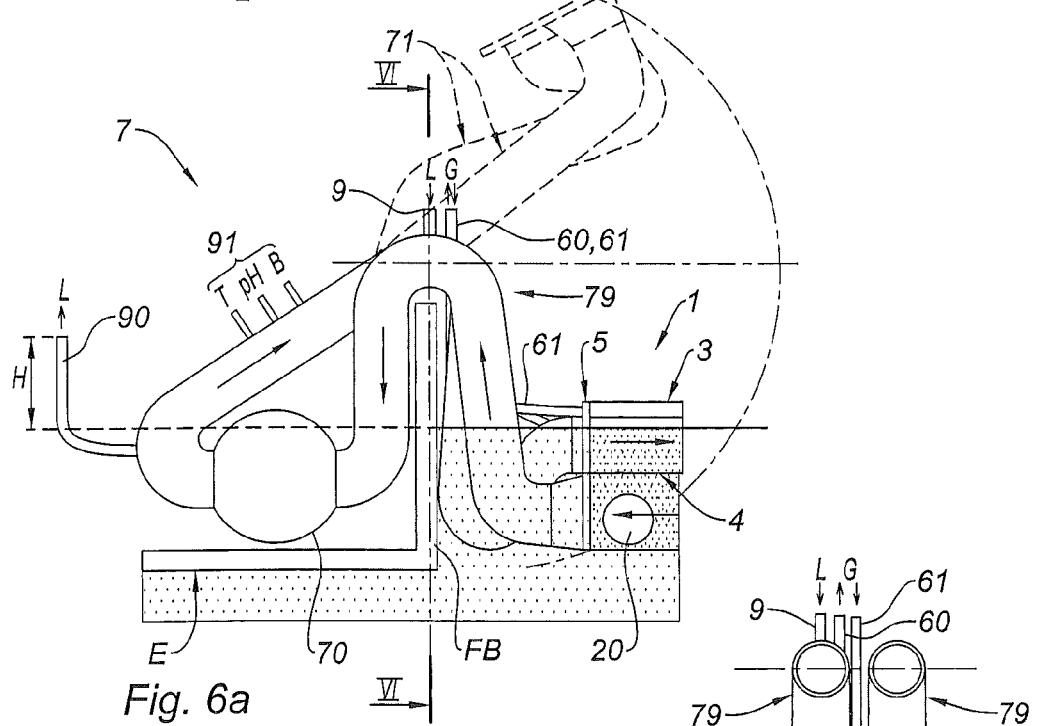
FIG. 6a is a partial diagrammatic profile view of a reactor according to the invention comprising a closing channel integrating means for making the liquid medium circulate according to a first embodiment.

The communication point of this outlet channel 90 of the liquid L with the closing channel 7 is placed as far as possible from and preferably upstream of the injection point(s) 9 of the sterile liquid medium L, as illustrated in FIGS. 6a and 7a, the arrows showing in the figures the circulation direction of the liquid medium L. It is in fact at the outlet of this outlet channel 90 that the culture is harvested and it is necessary to avoid short circuits that would dilute it.

This outlet channel 90, forming a spillway, constitutes a break of the confinement of the liquid culture medium L. To avoid retro-contamination of the culture in progress, the outlet channel 90 can usefully have a length of several meters and be kept sterile by periodic cleaning.

Figure 4:
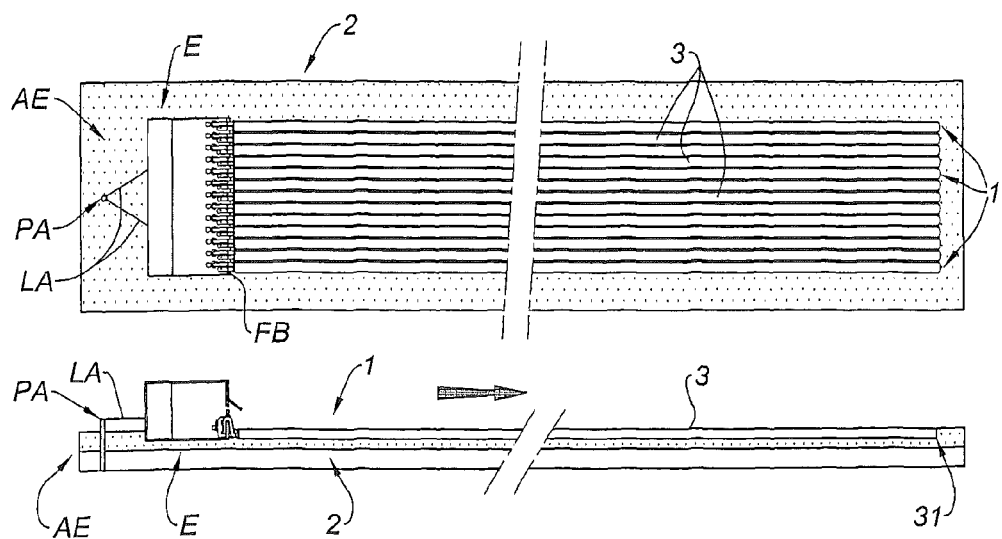
FIG. 4 is a top profile diagrammatic view illustrating a reactor according to the invention including several jackets moored only on one side of a floating craft.
Figure 5:
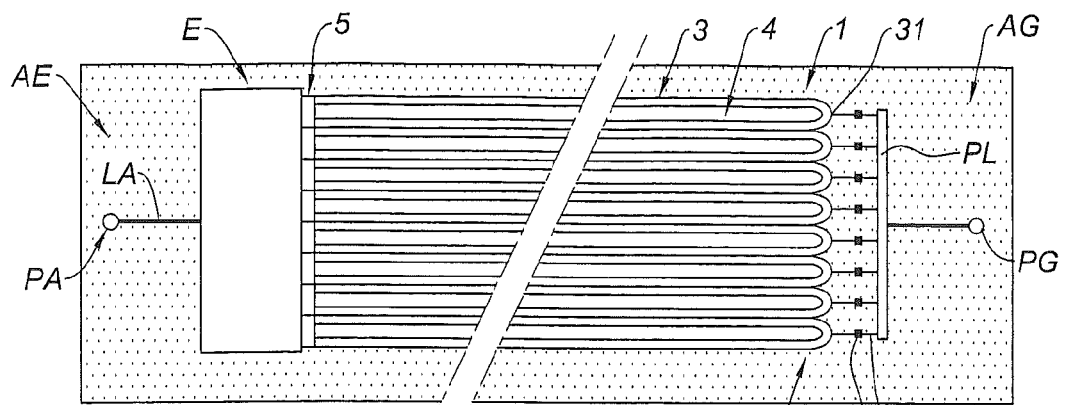
FIG. 5 is a top diagrammatic view illustrating another reactor according to the invention including several jackets moored on two sides of a craft and a foot rudder and swivel system, respectively.

As shown in FIGS. 4, 5 and 11, the closing channel 7, the circulation means 8, and the plate 5 are fastened on a craft E resting on the water, this craft E possibly being of the floating type and able to form a floating craft or barge, or possibly being of the pontoon type with beams or baulks driven into the bottom of the expanse of water.

This craft E can comprise a closed space, or ceiling space, in which are positioned, sheltered from bad weather, the closing channel 7 and the circulation means 8, and a wall or freeboard FB on which the sheaths 3, 4 are fastened to said craft E via the plate 5; the distal ends 31, 41 of these sheaths 3, 4 being left free, which allows them to align themselves in the direction of the relative movement of the water mass that supports the assembly, and results in reducing the draft forces related to the movement of said water mass support. Such a productive assembly optimizes the use of shared means such as the craft E and the onboard functionalities.

In the embodiments illustrated in FIGS. 4 and 11, the craft E is floating and moored in the bottom of the expanse of water, here fairly shallow, by a single mooring AE of the craft E, such that the outer sheaths 3 of the jackets 1 can align themselves in the current field caused by the wind from this craft E freely oscillating around its single mooring AE. This mooring AE comprises a mooring point PA, made in particular in the form of a beam or a rod vertically driven into the bottom of the expanse of water, and mooring connections LA connecting the craft E to the mooring point PA and leaving said craft E freely rotating around the mooring point PA. When the mooring AE is done at a single point PA, as in the case of the embodiments illustrated in FIGS. 4 and 11, it is necessary to provide enough space for the assembly to be able to swing around this point under the influence of the currents, and in particular those caused by the wind.

In another embodiment illustrated in FIG. 5, the distal ends 31 of the outer sheaths 3 are moored in the bottom of the expanse of water, here fairly shallow, by a mooring AG of the outer sheaths 3, such that the outer sheaths 3 of the jackets can no longer align themselves in the current field caused by the wind.

This mooring AG comprises connections LG connecting the distal ends 31 of the outer sheaths 3 to a shared foot rudder PL perpendicular to the outer sheaths 3 deployed and floating horizontally on the water, and a mooring point PG, made in particular in the form of a beam or rod vertically driven into the bottom of the expanse of water, to which the foot rudder PL is connected. These connections L advantageously include rotary hinges AR, in particular of the swivel type, such that the outer sheaths 3 can rotate freely around their respective longitudinal axes, as described above.

Adjusting the length of the connections LG and their parallel positioning makes it possible to distribute the mooring forces uniformly between all of the outer sheaths 3 and to allow their rotation or oscillation in order to clean their respective outer walls 31, as described above; the rotation of the outer sheaths 3 being made possible by the assembly of rotary hinges AR on these connections LG between the distal ends 31 of the outer sheaths 3 and the foot rudder PL.

In the case where the water plane is navigable, day and night signaling means in accordance with local laws can equip the different points of this floating assembly, and in particular the distal ends 31 of the outer sheaths 3.

Figure 6B:
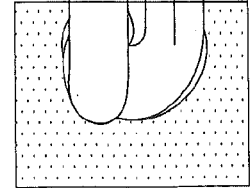

In the embodiments illustrated in FIGS. 6, 7 and 12, the closing channel 7 has a housing 70 (visible in FIGS. 6a, 7, 12, and 13a), with a broadened section, intended to partially receive the circulation means 8. This housing 70 extends in a horizontal primary direction, as shown in FIG. 6a, or a vertical one, as shown in FIGS. 7 and 12.

In the embodiment illustrated in FIGS. 7a to 7d, the circulation means 8 is made in the form of a mechanical propulsion means that comprises a propeller 80 driven in rotation by a rotary engine 81 via an output shaft 82 of said engine 81. The engine 81 is arranged outside the reactor 2 and the output shaft 82 sealably passes through the closing channel 7 to emerge inside the housing 70 and support the propeller 80, which is thus able to move in rotation inside said housing 70.

Advantageously, the housing 70 of the propeller 80 is positioned between a divergence zone and a convergence zone of the closing channel 7 of the liquid culture medium L, so as to ensure hydraulic continuity without abrupt speed variation, with the aim of limiting the energy losses, accelerations, and shear stresses undergone by the microorganisms.

According to one advantageous feature and as illustrated in FIGS. 7 and 12, the housing 70 is positioned a vertical rising branch of the closing channel 7, and therefore the propeller 80 has a vertical axis of rotation, in order to allow the evacuation of the gas G that can form in the housing 70 and thereby avoid cavitation phenomena.

Moreover, and as shown in FIG. 7, the position of the gas G exhaust means 60 upstream of the circulation means 8, or of the propeller 80, combined with the position of the circulation means 8 in the housing 70 upstream of the gas injection means 61, is also advantageous to prevent the gas from circulating through the propeller 80 and harming its operation. In fact, the presence of gas G hinders the operation of most of the mechanical propulsion means and the propellers in particular, and its accumulation must therefore be avoided at the risk of causing the propeller 80 to cavitate.

In the embodiment illustrated in FIGS. 6, 7 and 11, the closing channel 7 has two curved portions 79, an outbound portion and a return portion, respectively, arranged on either side of the housing 70 for receiving the circulation means 8. These curved portions 79, or gooseneck portions, have a curvature of substantially 180° in order to achieve the clearing of the wall or freeboard FB of the craft E; such clearing guaranteeing the isolation of the circulation means 8 with regard to the water and also the safety of the reactor and of the people using said reactor.

Moreover, and as illustrated in FIGS. 6a and 11, these curved portions 79 can be movable in part in a raised position in order to be able to take water out and raise the connecting plate 5 of the sheaths 3, 4, in particular to allow placement of the sheaths 3, 4 outside the water and under aseptic conditions.

The placement of the flexible sheaths 3, 4 is described hereinafter in reference to FIGS. 11a and 11b. The sheaths 3, 4 can be delivered in the form of drums B, where a float F is positioned at the center of the drum B to stabilize its flotation on the expanse of water.

Figure 11A:
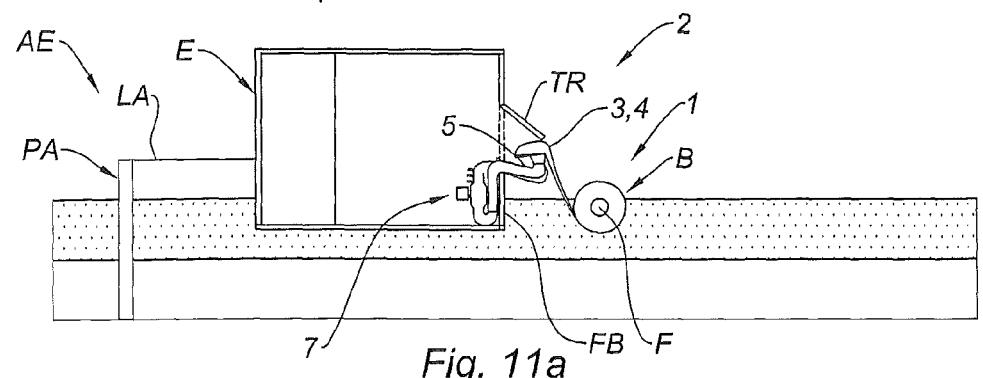
FIGS. 11a and 11b are diagrammatic profile views of a reactor according to the invention including a jacket moored on one side of a floating craft, illustrating a step for placing the jacket on the closing channel and a step for deployment of the jacket on the expanse of water by inflation or filling, respectively.
Figure 11B:
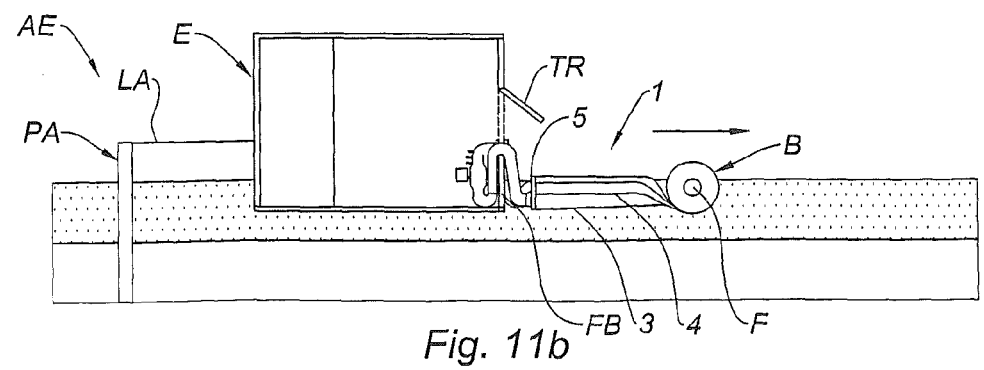

As visible in FIG. 11a, the two sheaths 3, 4 are mounted on the plate 5 at their respective proximal ends 30, 40, said plate advantageously occupying a raised position as described above. This operation for fastening the sheaths 3, 4 on the plate 5 is done aseptically to avoid introducing contaminants into the culture medium.

As visible in FIG. 11, the plate 5 is lowered and partially submerged in the water, then the deployment of the sheaths 3, 4 is done by filling using sterile liquid L and gaseous G mediums. The liquid and gas arrival can opportunely occur through all of the openings 11, 12 formed in the plate 5. Indeed, in the contrary case, only the liquid L and gas G inlet sheath receives the fluids and undergoes the deployment forces. Once the sheathes 3, 4 are unwound and inflated, the circulation of the liquid medium L can be established in the reactor 2, by setting the circulation means 8 in motion.

A flap TR can be provided on the craft E in order to isolate the outer part of the reactor 2 from the inner part of said reactor 2 once the sheaths 3, 4 are unwound and inflated.

Figures 8A, 8B:
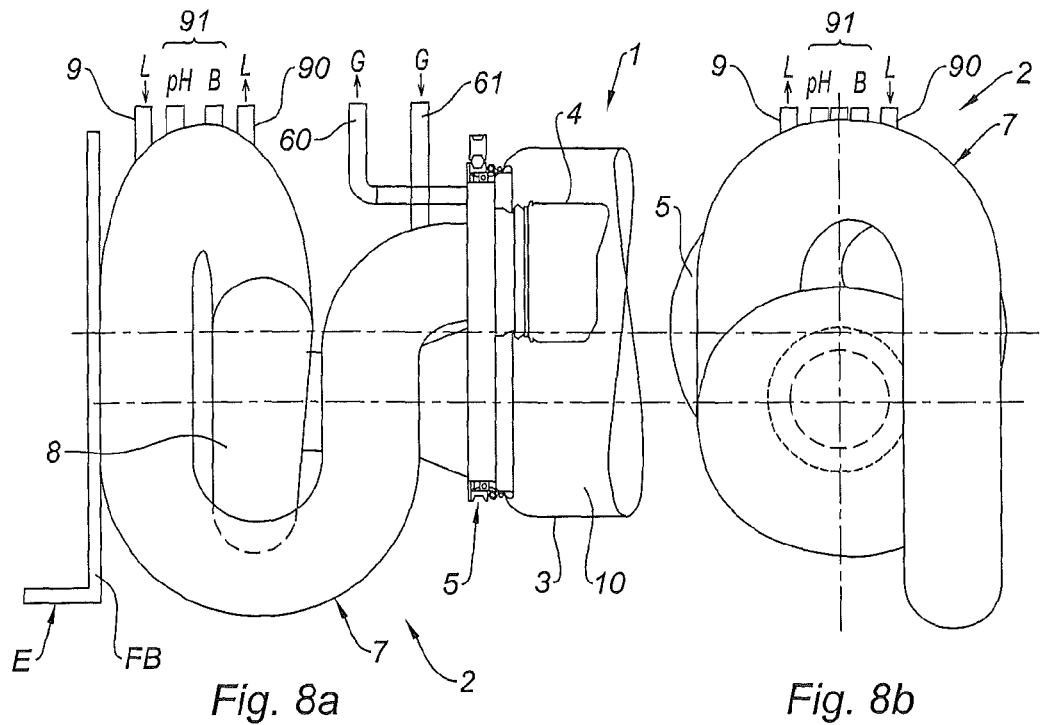
Figures 9A, 9B:
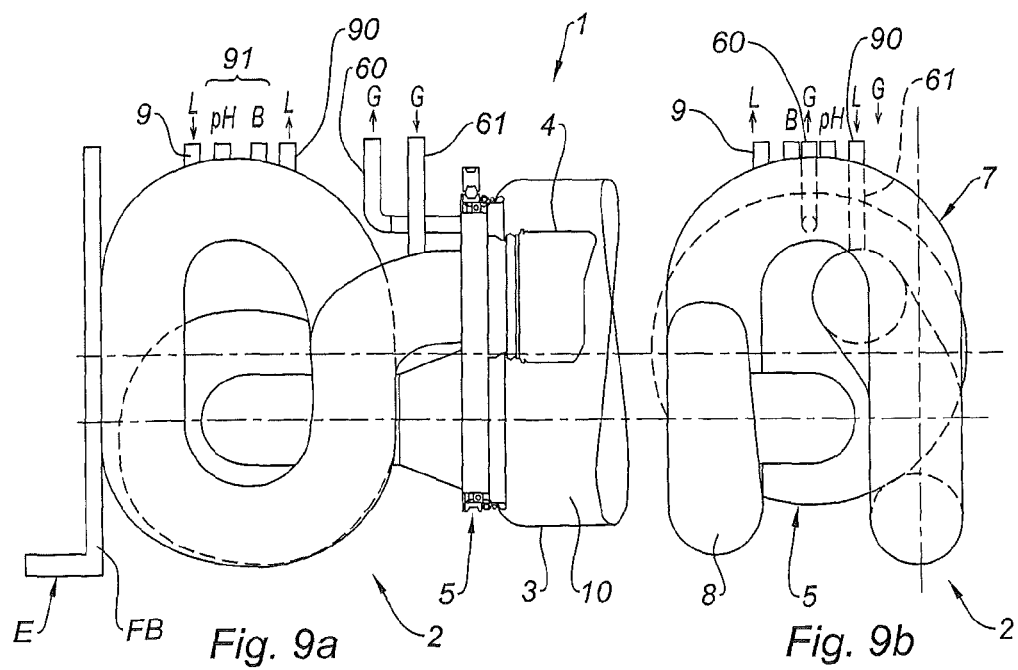

In the embodiments illustrated in FIGS. 8 and 9, the circulation means is made in the form of a centrifugal pump 8, the assembly being positioned outside the craft E; this is called an off board solution that has the advantage of compactness but the drawback of being aggressive for the microorganisms. The cleaning body passage 20, described below, requires a closing channel 7 having an open wheel and a volute with a large diameter that reduce the effectiveness. In the embodiment illustrated in FIG. 8, the volute is of the frontal volute type, and in the embodiment illustrated in FIG. 9, the volute is of the sagittal volute type. In these embodiments with a centrifugal pump, the plate 5 is integral with a craft E or a dock, and may possibly be raised to facilitate the placement of the sheaths 3, 4 outside the water.

As shown in FIGS. 1, 6a, 7a, 7d and 12b, the reactor 2 can also comprise one or several cleaning bodies 20 configured to circulate along the flow path, in other words inside the inner sheath 4, the inter-sheath space 10 and the closing channel 7, in order to clean the inside of the sheaths 3, 4 and the closing channel 7. To be able to circulate in a loop in the reactor 2, the cleaning body or bodies 20 are also configured to go through the circulation means 8 of the liquid culture medium, for example through the blades of the propeller 80 in the particular embodiment described above in reference to FIG. 7.

The cleaning body or bodies 20, preferably spherical, for example have a diameter substantially equal to the inner diameter of the closing channel 7 to optimize the cleaning of the inner walls of the closing channel 7.

The cleaning body or bodies 20 also have the aim of completing the cleaning of the inner wall 34 of the outer sheath 3 and the outer wall 43 of the inner sheath 4 done with the free movement of the inner sheath 4 inside the outer sheath 3; this free movement being favored by the rotary fastening of the outer sheath 3 on the plate 5.

The speed difference between the gaseous circulation and the liquid circulation directly affects the gas/liquid mass transfers and must advantageously be kept at the highest level possible. This is why each cleaning body 20 must not prevent the passage of the gas. To that end, each cleaning body 20 is configured to at least partially allow the gas circulating inside the reaction channel 2 to pass while being adapted to be driven by the circulation of the liquid culture medium so that the cleaning body 20 does not influence the speed difference between the gas and the liquid medium.

To that end, the or each cleaning body 20 is made in the form of a brush, in particular spherical, comprising a set of bristles, hairs, strands or equivalent means, with a central portion carrying these bristles. Thus, in the horizontal sheathes 3, 4, the emerged bristles allow the gas to pass at the gas ceiling and the submerged central portion carrying the bristles has a large enough diameter to constitute an obstacle to the passage of the liquid, such that the liquid medium brings the cleaning body 20 with it.

Likewise, the cleaning body 20 can be made in the form of a hollow sphere in an elastomer material whereof a substantial portion of the surface is pierced with holes that make it possible to allow the gas to pass.

Figure 10A:
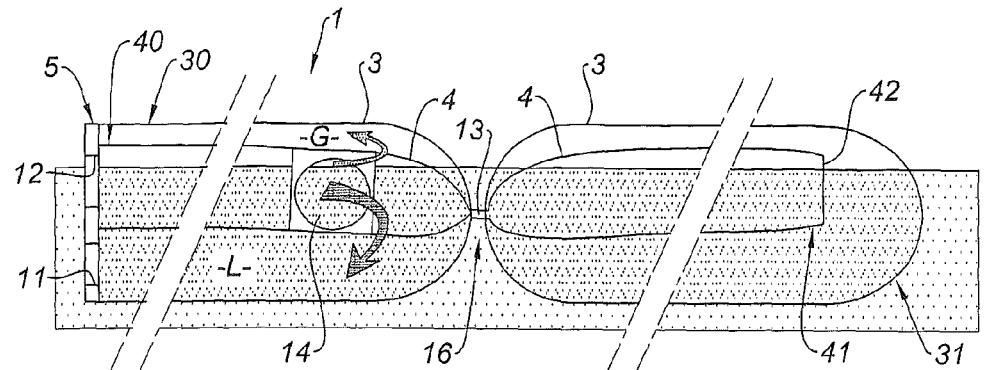
FIGS. 10a and 10b are diagrammatic longitudinal cross-sectional views of a jacket according to the invention, illustrating a clipping step of the jacket to culture only a reaction sub-volume of the jacket, and a step for removing the clipping means in order to culture the entire jacket, respectively.
Figure 10B:
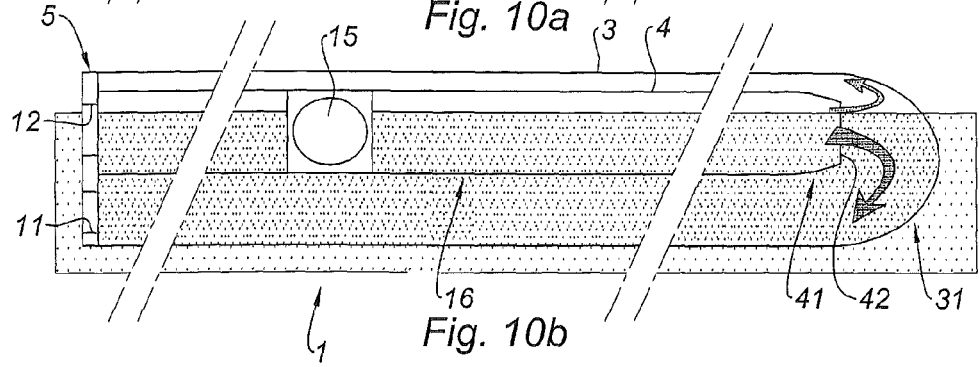

In one particular embodiment of the invention illustrated in FIGS. 10*a* and 10*b*, the jacket 1 also comprises:

removable clipping or binding means 13 designed to clip or bind the two sheaths 3, 4 on an intermediate area 16 situated between the respective proximal 30, 40 and distal 31, 41 ends of the two sheaths 3,4;

at least one intermediate communication orifice 14 between the inside of the inner sheath 4 and the inter-sheath space 10, said intermediate communication orifice 14 being provided on the inner sheath 4 between its proximal end 40 and said intermediate clipping or binding area 16; and means 15 for closing said intermediate communication orifice 14, in particular of the flap type, said closing means 15 being able to move between an open position (illustrated in FIG. 10*a*) and a closed position (illustrated in FIG. 10*b*).

Thus, the inner sheath 4 comprises a flap 15 that can be maneuvered from the outside of the outer sheath 3 to open or close said intermediate orifice 14.

The intermediate clipping or binding area 16 is positioned at about one tenth of the length of the outer 3 or inner 4 sheath, so as only to exploit a reaction sub-volume, corresponding to the portion of the jacket 1 and the sheaths 3, 4 situated between the plate 5 and this intermediate area 16, and that can represent about ¹⁄₁₀ of the total volume of the jacket 1; this ratio corresponding to that of the inoculation volume attached to the culture volume traditionally used.

Firstly, illustrated in FIG. 10*a*, the clipping or binding means 13 clips or binds the two sheaths 3, 4 on the intermediate area 16 situated beyond the intermediate orifice 14, thereby isolating the reaction sub-volume. The sheaths 3, 4 are filled with sterile nutritional medium and gas and the flap 15 formed in the inner sheath 4 is opened so as to allow the passage of the gas G and liquid L at the end of said reaction sub-volume. In this way, this sub-volume has all of the functionalities of the entire volume and can operate autonomously. It is thus possible to inoculate and culture it.

Secondly, illustrated in FIG. 10*b*, when the concentration reaches a sufficient level in this sub-volume, the clipping or binding means 13 is removed and the flap 15 is closed, such that the rest of the volume is put on line and thereby inoculated by the sub-volume, the reactor then assuming its full production capacity.

Figure 12A:
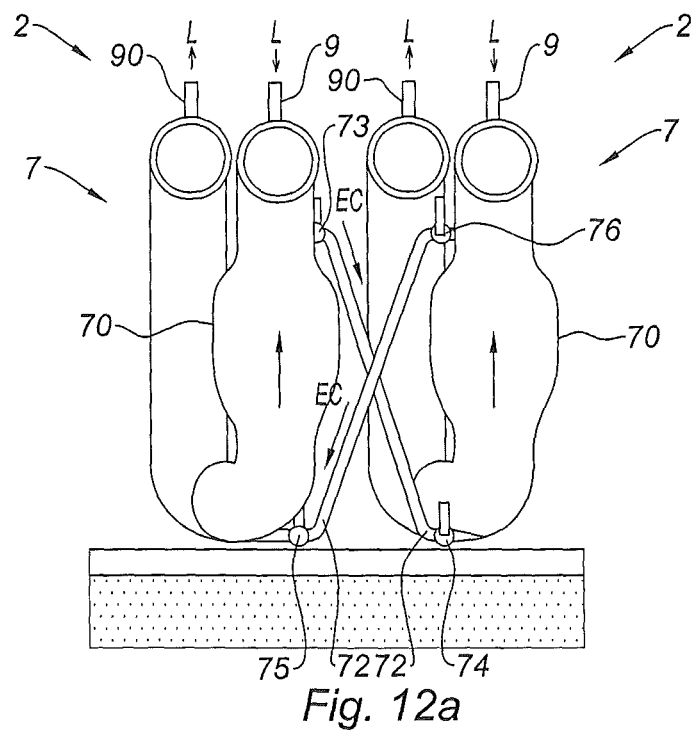
FIG. 12a is a diagrammatic transverse cross-sectional view of two reactors according to the invention and connected to each other via connecting channels.
Figure 12B:
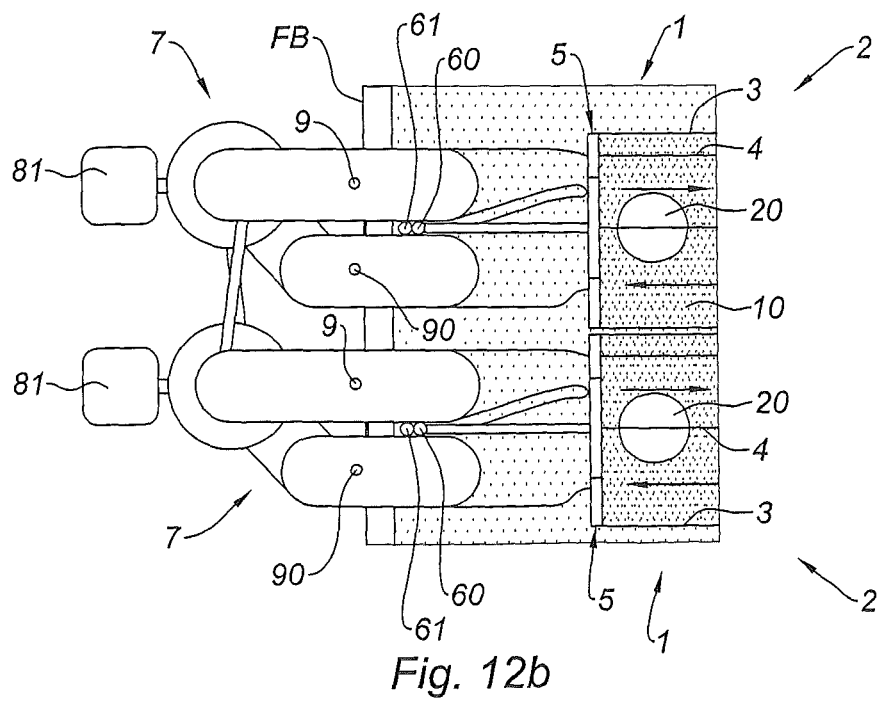

As illustrated in FIGS. 12*a* and 12*b*, the invention also concerns a set of photosynthetic reactors comprising at least two reactors 2 according to the invention, namely first (on the left) and second (on the right) reactors, and comprising at least one connecting channel 71, 72 ensuring a fluid connection between the first reactor and the second reactor and at least one valve 77, 78 positioned on said connecting channel 71, 72, in order to allow the inoculation of one reactor by the other reactor. It is thus possible to interconnect two reactors such that their contents are exchanged, in order to make the inoculation of one reactor possible by the other whereof the concentration has reached an advanced stage.

In the embodiment illustrated in FIGS. 12*a* and 12*b*, the assembly comprises two connecting channels 71, 72 between the two reactors 2. The connecting channels 71, 72 are provided, at their respective ends, with valves 73, 74, respectively, for the connecting channel 71 and 75, 76, respectively, for the connecting channel 72.

The first connecting channel 71 connects an inlet point positioned on the first reactor 2 downstream of the housing 70 for receiving the circulation means, such as the rotary propeller (not shown), to an outlet point positioned on the second reactor upstream of the housing 70 for receiving the circulation means of said second reactor 2.

The second connecting channel 72 connects an inlet point positioned on the second reactor 2 downstream of the housing 70 for receiving the circulation means, such as the rotary propeller (not shown), to an outlet point positioned on the first reactor upstream of the housing 70 for receiving the circulation means of said second reactor 2.

The reactors 2 are assembled in a parallel manner so as to form a coherent productive assembly. To make the inoculation of one reactor by its neighbor, whereof the microorganism concentration has reached an advanced stage, possible, the assembly provides for interconnecting these two reactors with the connecting channels 71, 72 such that their respective contents are mixed.

Moreover, as visible in FIG. 12*a*, the outlet points of the connecting channels 71, 72 are placed at the end of the convergence areas situated upstream of the corresponding housing 70 to benefit from a Venturi effect.

The valves 73, 74, 75, 76 enable the connection under aseptic conditions of the two connecting channels 71, 72 that connect, in a crossed and symmetrical manner, the inlet points and the outlet points of the two reactors 2 to be interconnected. The valves 73, 74, 75, 76 are positioned substantially at the inlet and outlet points of the corresponding connecting channels 71, 72.

Such an assembly can be used as follows to proceed with the inoculation of the second reactor 2 (on the right) from the first reactor 2 (on the left) already in use when the microorganism concentration has reached the operating level.

Firstly, the valves 73, 74 and their opposites 75, 76 are closed, the first reactor 2 is in use with the establishment of the circulation inside this first reactor, and the second reactor 2 to be inoculated is filled with sterile nutritional medium.

Secondly, the circulation is established inside the second reactor 1B and the valves 73, 74 and their opposites 75, 76 are opened to establish a cross-exchange between the two reactors as illustrated by arrows EC of FIG. 12a.

After opening the valves 73, 74 and their opposites 75, 76, the concentrations become substantially equal in the two reactors 2 and it is possible to isolate them by closing the valves 73, 74 and their opposites 75, 76. To reduce the duration of this exchange, a pump (not shown) can be inserted on one and/or the other of the connecting channels 71, 72.

Figure 13A:
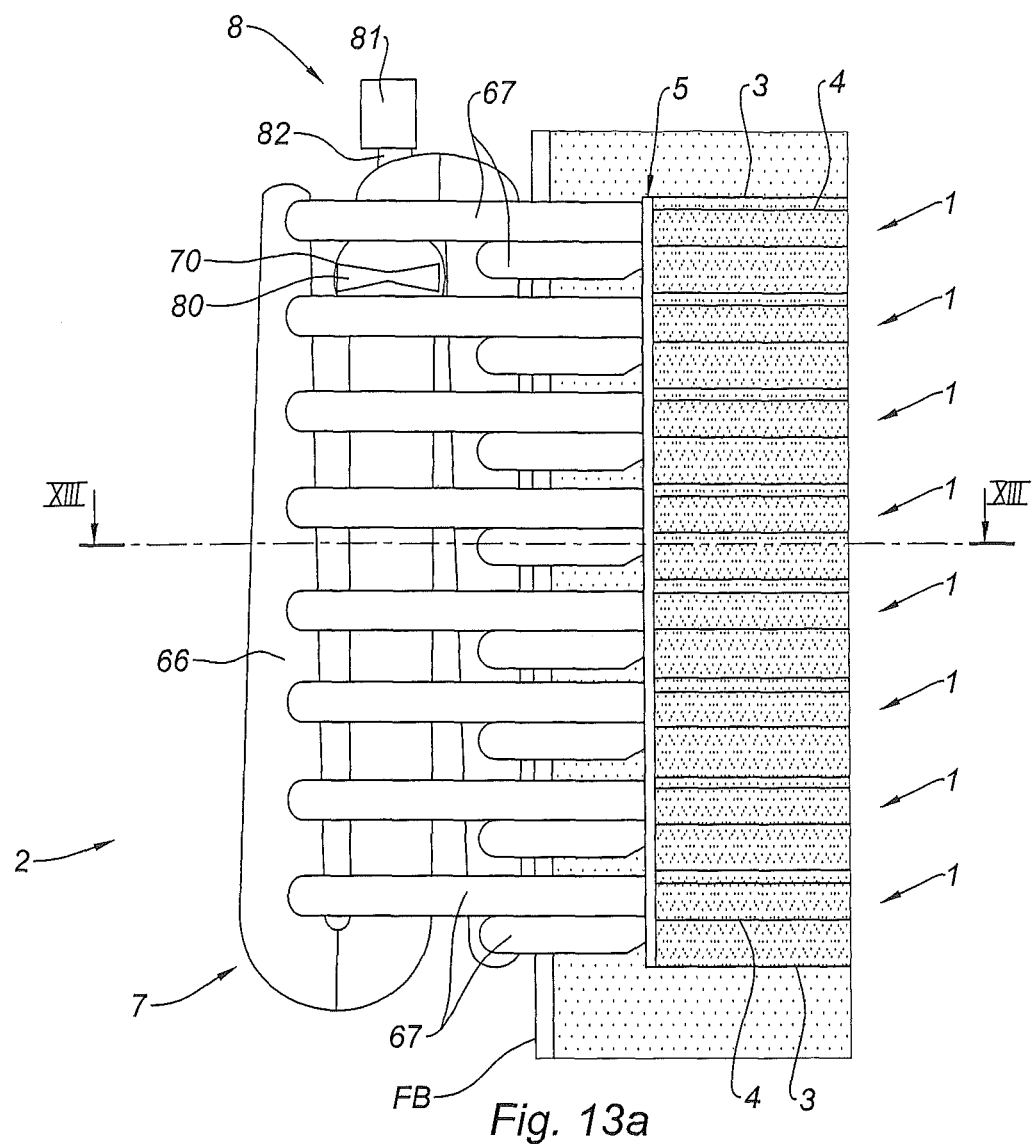
FIG. 13a is a partial diagrammatic top view of a reactor including several reaction jackets connected to a closing channel, integrating a circulation means, shared by all of the jackets.
Figure 13B:
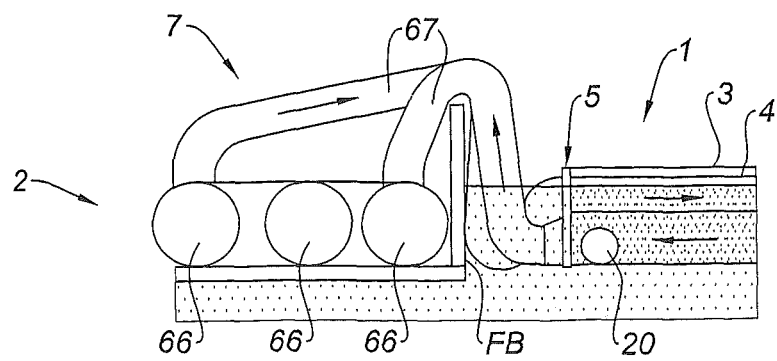

As illustrated in FIGS. 13a and 13b, the invention also concerns a reactor 2 including a plurality of reaction jackets 1 connected in parallel on connecting plates 5, this reactor 2 comprising a single and same closing channel 7 having a housing 70 for receiving a circulation means 8, such as a propeller 80/rotary engine 81 system, and a plurality of connecting ducts in fluid connection with the jackets 1.

In this particular embodiment, which includes interconnecting reaction jackets 1 in parallel, the interest lies in sharing certain functionalities, such as the circulation means the regulation means, but with the drawback of increasing exposure to accidents, and in particular contamination.

In this embodiment, the closing channel 7 includes a collecting duct 66 in which the housing 70 is provided for receiving the circulation means 8, and a plurality of distribution ducts 67 connected, on one hand, to the collecting duct 66 and, on the other hand, to the respective jackets 1, such that the liquid medium is collected as output of the jackets 1, passes into the circulation means, then is distributed at the inlet of the jackets 1. Opportunely, the distribution is done in the same order as the collection so as to make the flow rates uniform in the jackets 1.

Opportunely, and in order to keep the speeds as uniform as possible, the collection duct 66 and the distribution ducts 67 have a variable section, decreasing from one end to the other of the channel they form.

The method for growing photosynthetic microorganisms, in particular algae, using a reactor 2 according to the invention comprises the following steps:

injecting a liquid culture medium into the reaction jacket 1 at a rate controlled with the liquid injection means 9;

injecting a gas G into the reaction jacket 1 at a rate controlled with the gas injection means 61;

pressurizing the outer sheath 3 of the jacket 1 including creating an excess inflation pressure in said outer sheath 3 to ensure the buoyancy of said outer sheath 3 and its deployment;

circulation of the liquid culture medium with the circulation means 8;

control of the circulation means 8 and the gas injection means 61 to establish, in the reaction jacket 1, a gas/liquid culture medium diphasic flow state of the stratified or slug or elongated bubbles type; and recovering photosynthetic microorganisms with the outlet channel 90.

During the travel in the jacket 1, the liquid medium containing the photosynthetic microorganisms receives the solar radiation through the transparent material of the sheaths 3, 4, exchanges heat with the water plane by diffusion, mixing and conduction through this same material, and exchanges components with the gas G through their shared interface. The production capacity depends above all on the length of the sheaths 3, 4 of the jacket 1; several jackets 1 being able to be usefully positioned in large numbers next to each other to ensure the essential cleaning function described above.

Advantageously, the circulation speed of the gas is established between about 0.5 and 1.5 m/s, corresponding to an adequate speed state for the flow rates necessary for the reaction.

Also advantageously, the circulation means 8 comprises a propeller 80 driven in rotation by an engine 81 and the rotational speed of the propeller 80 is less than about 100 revolutions per minute, in order to limit the mechanical stresses within the liquid culture medium.

Figure 14:
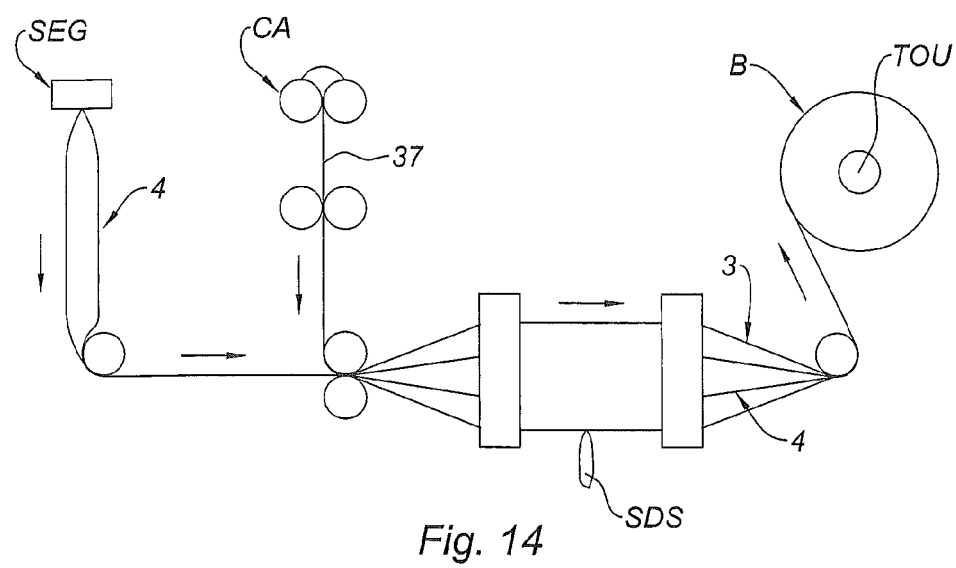
FIG. 14 is a diagrammatic view illustrating a system for manufacturing a jacket according to the invention.

The invention also concerns a method for producing a jacket 1, described in reference to FIG. 14, comprising the following steps:

making the inner sheath 4 by an extrusion method of a plastic material and inflating the extruded plastic, also called inflation extrusion method using an extrusion inflation system SEG;

making an outer sheet 37 from a plastic material, in particular by a calendering method using a calender CA;

surrounding the inner sheath 4 with the outer sheet 37 up to a junction of two opposite longitudinal edges of the outer sheet 37;

welding the outer sheet 37 along its two opposite edges joined during the surrounding step, using a welding system SDS, so as to form the outer sheath 3 surrounding the inner sheath 4; and winding the two sheaths 3, 4 one around the other on a single reel TOU, so as to form a drum B.

The sheaths 3, 4 are produced and positioned one in the other in the workshop before delivery. This method responds to the issue of introducing one very long sheath into another one by proposing a simultaneous and continuous production of these two sheaths 3, 4, preferably aseptically so as to reduce the risks of initial contamination of the cultures.

This production method, which includes closing the outer sheath 3 around the inner sheath 4, makes it possible to equip this inner sheath 4 during assembly, in particular with a communication orifice 42 and possibly with the intermediate orifice 14 provided with its flap 15.

The winding of the two sheaths 3, 4 positioned one in the other begins with their distal ends before the deployment or unwinding described above in reference to FIGS. 11a and 11b. The outer sheath 4 is closed at its distal end, as described above, and this distal end may be equipped with a system for hooking a connection, such as the connection LG described above in reference to FIG. 5.

Opportunely, the thickness of the film making up the sheaths 3, 4 can evolve from the distal end to the proximal end to increase the resistance at the same time as the forces exerted on the film.

Of course, the embodiment described above is in no way limiting and other improvements and details can be made to the jacket, reactor and methods according to the invention, without going beyond the scope of the invention where other forms of the outer sheath and/or inner sheath and/or connecting plate and/or closing channel can for example be made.

Figure 15:
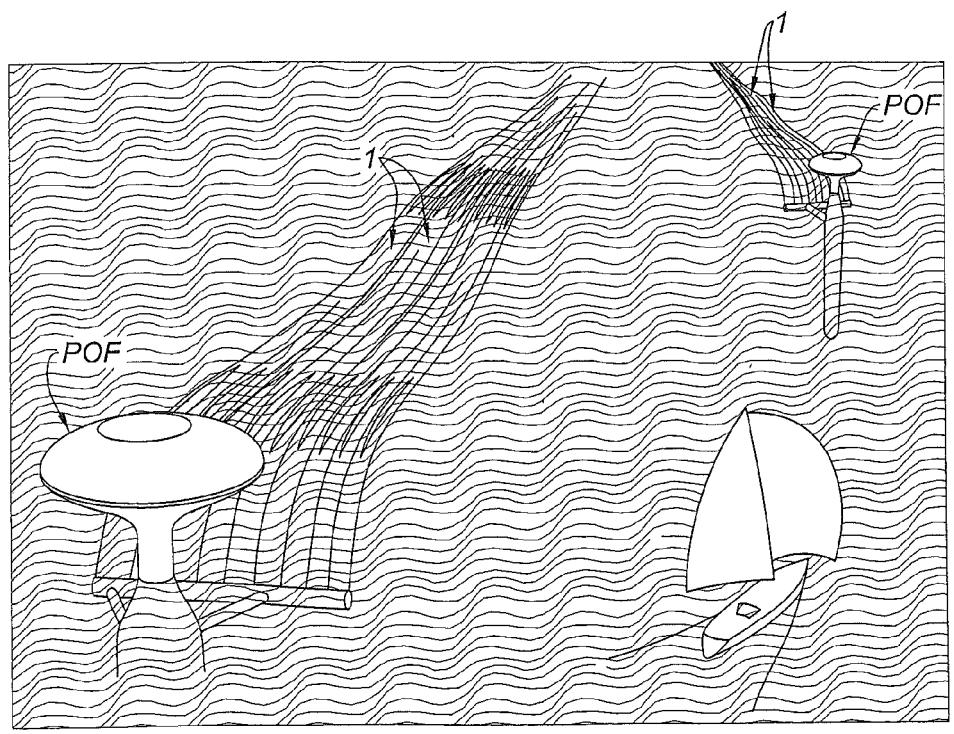
FIG. 15 is a diagrammatic perspective view of reactors according to the invention including jackets moored on an offshore platform.

It is thus possible to consider, as diagrammatically illustrated in FIG. 15, providing for mooring of the jackets 1 on an offshore platform POF on the open sea. This offshore platform POF constitutes a floating service structure that can for example receive a crew and the operation of which is preferably fully automated.

The offshore platform POF is preferably made up of a Froude buoy, not very sensitive to surface agitation. In this case, the submerged part of the buoy contains the buoyancy reserves in the upper part, the ballast in the bottom part and the functionalities and storage in the intermediate levels.

On this offshore platform POF it is also possible to provide a structure supporting the connecting plates of the sheaths of the jackets 1, which is connected to an offshore platform POF by one or two arms whereof the incline can be adjusted; this structure supporting the connecting plates thus being able to be brought to the surface to operate on the plates or to be submerged in the normal operating mode.

Other activities, such as fish-rearing, can be associated with this offshore platform POF. Bow nets for confining the cultivated fish can for example be placed under the sheet of the jackets 1 floating on the surface of the sea.

Moreover, it is also possible to consider the offshore platform POF being provided with propulsion means, potentially automated, so that it moves to follow the surface temperatures most adapted to the growth of photosynthetic microorganisms, escape the most unfavorable meteorological conditions, and avoid collisions. The movements of the offshore platform POF are controlled in situ or from the ground according to weather and radar information to look for the best routes. The offshore platform POF can also approach the coast to unload its product and to be refueled.

The invention claimed is:

1. A reaction jacket for a photosynthetic reactor adapted for growing photosynthetic microorganisms, said reaction jacket configured to float on an expanse of water and comprising a first and a second openings, said reaction jacket delimiting a reaction channel for channeling a gas/liquid culture medium two-phase flow path between the first and second openings of said reaction jacket, said reaction jacket comprising two sheaths, outer and inner, respectively, made at least partially from a material transparent to light radiation, the inner sheath extending to an inside of the outer sheath such that said sheaths define an inter-sheath space between them in fluid connection with the first opening of the reaction jacket, wherein the outer sheath has an open proximal end and a closed distal end, and the inner sheath has an open proximal end in fluid connection with the second opening of the reaction jacket and a distal end provided with at least one communication orifice between the inside of the inner sheath and the inter-sheath space, the two sheaths delimiting said reaction channel forming a round trip journey between said first and second openings, inside the inter-sheath space and inside the inner sheath via the communication orifice formed at the distal end of the inner sheath wherein said reaction jacket further comprising:
an outer connecting piece on which the proximal end of the outer sheath is hermetically mounted, and on which the first opening of the reaction jacket is formed in fluid connection with the inter-sheath space; and
an inner connecting piece on which the proximal end of the inner sheath is hermetically mounted, and on which the second opening of the reaction jacket is formed in fluid connection with the proximal end of the inner sheath.

2. The jacket according to claim 1, wherein at least one of the two sheaths is made from a flexible material adapted to allow folding, inflation, transverse deformation and bending of said sheath.

3. The jacket according to claim 2, further comprising:
a removable clip for binding the two sheaths on an intermediate area situated between the respective proximal and distal ends of the two sheaths;
at least one intermediate communication orifice between the inside of the inner sheath and the inter-sheath space, said intermediate communication orifice being provided on the inner sheath between its proximal end and said intermediate binding area; and
a closing device for closing said intermediate communication orifice, said closing device being able to move between an open position and a closed position.

4. The jacket according to claim 1, wherein the proximal end of the inner sheath is rotatably mounted on the inner connecting piece.

5. The jacket according to claim 1, wherein the inner connecting piece is mounted inside the outer connecting piece.

6. The jacket according to claim 1, wherein the outer connecting piece includes a coupling system for coupling said outer connecting piece to a driving element for driving said outer connecting piece in rotation so as to drive the outer sheath in rotation.

7. The jacket according to claim 5, wherein the inner connecting piece freely rotates in the outer connecting piece, so that rotation of the outer sheath ensures the rotation of the inner sheath by friction between the two sheaths.

8. The jacket according to claim 1, wherein the inner sheath extends over at least 90% of a length of the outer sheath.

9. The jacket according to claim 1, wherein the communication orifice, provided on the distal end of the inner sheath, has a convergence zone, comprising a reduction of a diameter of the inner sheath at the open distal end of the inner sheath, in order to achieve an energy loss in the gas/liquid culture medium two-phase flow.

10. The jacket according to claim 1, further comprising a third sheath in a flexible material extending inside the inner sheath so as to allow an injection or suction of gas at the distal ends of the two sheaths.

11. A photosynthetic reactor configured for growing photosynthetic microorganisms, comprising:
at least one reaction jacket according to claim 1;
at least one closing channel providing a fluid connection between the first and the second openings of said reaction jacket;
at least one circulation device positioned in said closing channel and configured to circulate a liquid culture medium in said closing channel.

12. A method for growing photosynthetic microorganisms comprising:
providing at least one photosynthetic reactor according to claim 11;
injecting the liquid culture medium into the reaction jacket at a controlled rate;
injecting a gas into the reaction jacket at a controlled rate;
circulating the liquid culture medium with the circulation device;
controlling the circulation of the liquid culture medium and the injection of the gas to establish, in the reaction jacket, a gas/liquid culture medium two-phase flow state of the stratified or slug or elongated bubbles type.

13. The method according to claim 12, wherein the controlling step comprises a step for controlling the circulation speed of the liquid in the reaction jacket between about 0.1 and 1.0 m/s.

14. The method according to claim 12, wherein the circulation device comprises a propeller driven in rotation by a motor, and the rotational speed of the propeller is less than about 1000 rpm.

* * * * *